US010725022B2

(12) United States Patent
Lütolf et al.

(10) Patent No.: US 10,725,022 B2
(45) Date of Patent: Jul. 28, 2020

(54) ARRAYS OF DISCRETE CELL CULTURE MICROENVIRONMENTS, METHODS OF MAKING SUCH ARRAYS AND USES THEREOF

(71) Applicant: ECOLE POLYTECHNIQUE FEDERALE DE LAUSANNE (EPFL), Lausanne (CH)

(72) Inventors: Matthias Lütolf, Tolochenaz (CH); Adrian Ranga, Ecublens (CH)

(73) Assignee: ECOLE POLYTECHNIQUE FEDERALE DE LAUSANNE (EPFL) EPFL-TTO, Lausanne (CH)

( * ) Notice: Subject to any disclaimer, the term of this patent is extended or adjusted under 35 U.S.C. 154(b) by 78 days.

(21) Appl. No.: 15/681,902

(22) Filed: Aug. 21, 2017

(65) Prior Publication Data
US 2018/0113114 A1 Apr. 26, 2018

Related U.S. Application Data

(62) Division of application No. 14/889,453, filed as application No. PCT/EP2014/059501 on May 8, 2014, now abandoned.

(30) Foreign Application Priority Data

May 8, 2013 (EP) .................... 13166952

(51) Int. Cl.
G01N 33/50 (2006.01)
(52) U.S. Cl.
CPC ....... G01N 33/502 (2013.01); G01N 33/5005 (2013.01); G01N 33/5073 (2013.01)
(58) Field of Classification Search
None
See application file for complete search history.

(56) References Cited

U.S. PATENT DOCUMENTS

2006/0188940 A1 8/2006 Cima et al.

FOREIGN PATENT DOCUMENTS

RU 2280459 1/2005
WO 0069449 11/2000
(Continued)

OTHER PUBLICATIONS

Sanborn, Tracy J; et al; "In situ crosslinking of a biomimetic peptide-PEGhydrogel via thermally triggered activation of factor XIII" Biomaterials, 23, 2703-2710, 2002 (Year: 2002).*

(Continued)

Primary Examiner — David W Berke-Schlessel
(74) Attorney, Agent, or Firm — David & Bujold PLLC; Michael J. Bujold

(57) ABSTRACT

A method of making an array having discrete volumes of cell culture micro-environments possessing different properties influencing the behavior of encapsulated cells, in particular proliferation, colony-formation, differentiation, migration, or combinations thereof. The method comprises a) providing different hydrogel precursor molecules, where the precursor molecules are linear or branched hydrophilic polymers for building up cell culture micro-environments; b) combining and dispensing different combinations of the hydrogel precursor molecules, according to step a), onto discrete volumes of a multi-well plate; c) adding one or more biologically active molecules to the discrete volumes and either attaching the molecules to one of the hydrogel precursor molecules present or a hydrogel, formed in step e), or allowing them to diffuse freely; d) adding cells onto/into the discrete volumes of the multi-well plate; and e) crosslinking the hydrogel precursor molecules based on an enzymatically catalyzed reaction or a Michael addition reaction to form a hydrogel matrix.

4 Claims, 8 Drawing Sheets

(56) References Cited

FOREIGN PATENT DOCUMENTS

| WO | 2010075933 A1 | 7/2010 |
|---|---|---|
| WO | 2011139993 A2 | 11/2011 |
| WO | 2011161172 A1 | 12/2011 |
| WO | 2013037836 A1 | 3/2013 |

OTHER PUBLICATIONS

Japanese Office Action issued in corresponding Japanese Patent Application No. 2016-512385 dated Mar. 20, 2018.
Peter J. Yang et al., Modulation of Mesenchymal Stem Cell Shape in Enzyme-Sensitive Hydrogels Is Decoupled from Upregulation of Fibroblast Markers Under Cyclic Tension, Tissue Engineering: Part A, vol. 18, Nos. 21 and 22, Nov. 1, 2012, pp. 2365-2375, © Mary Ann Liebert, Inc., See EP Search Report & International Search Report.
M. P. Lutolf et al., http://www.nature.com/naturebiotechnology, Synthetic biomaterials as instructive extracellular microenvironments for morphogenesis in tissue engineering, Nature Biotechnology vol. 23 No. 1 Jan. 2005, Published online Jan. 6, 2005, pp. 47-55.
M. P. Lutolf et al., www.pnas.org/cgi/doi/10.1073/pnas.0737381100, Synthetic matrix metalloproteinase-sensitive hydrogels for the conduction of tissue regeneration: Engineering cell-invasion characteristics, PNAS, Apr. 29, 2013, vol. 100, No. 9, pp. 5413-5418.
Ying Mei et al., www.nature.com/naturematerials, Combinatorial development of biomaterials for clonal growth of human pluripotent stem cells, Nature Materials, vol. 9, Sep. 2010, Published Online: Aug. 22, 2010, pp. 768-778, © 2010 Macmillan Publishers Limited.
Yoshinobu Murayama et al., Mouse zona pellucida dynamically changes its elasticity during oocyte maturation, fertilization and early embryo development, Human Cell 2006; 19, pp. 119-125, © 2006 The Authors, Journal compilation © 2006 Japan Human Cell Society.
Hitoshi Niwa et al., genesdev.cship.org, Self-renewal of pluripotent embryonic stem cells is mediated via activation of STAT3, Genes & Development 12, pp. 2048-2060, Edinburgh, UK, © 1998 by Cold Spring Harbor Laboratory Press.
Hitoshi Niwa et al., http://genetics.nature.com, Quantitative expression of Oct-3/4 defines differentiation, dedifferentiation or self-renewal of ES cells, nature genetics, vol. 24, Apr. 2000, pp. 372-376, © 2000 Nature America Inc.
J. Patterson et al., www.elsevier.com/locate/biomaterials, Enhanced proteolytic degradation of molecularly engineered PEG hydrogels in response to MMP-1 and MMP-2, Biomaterials 31, 2010, pp. 7836-7845, © 2010 Elsevier Ltd.
Wendy Prudhomme et al., www.pnas.org/cgi/doi/10.1073/pnas.0308768101, Multivariate proteomic analysis of murine embryonic stem cell self-renewal versus differentiation signaling, PNAS, Mar. 2, 2004, vol. 101, No. 9, pp. 2900-2905, © 2004 by The National Academy of Sciences of the USA.
Xiaoxia Qi et al., www.pnas.org/cgi/doi/10.1073/pnas.0401367101, BMP4 supports self-renewal of embryonic stem cells by inhibiting mitogen-activated protein kinase pathways, PNAS, Apr. 20, 2004, vol. 101, No. 16, pp. 6027-6032, © 2004 by The National Academy of Sciences of the USA.
Frederick Shatz et al., http://www.biolreprod.org, Human Endometrial Endothelial Cells: Isolation, Characterization, and Inflammatory-Mediated Expression of Tissue Factor and Type 1 Plasminogen Activator Inhibitor, Biology of Reproduction 62, 2000, pp. 691-697, © 2000 by the Society for the Study of Reproduction, Inc.
Karen L. Schmeichel et al., Modeling tissue-specific signaling and organ function in three dimensions, Journal of Cell Science 116, 2000, pp. 2377-2388, © 2003 The Company of Biologists Ltd.
Yoav Soen et al., www.molecularsystemsbiology.com, Exploring the regulation of human neural precursor cell differentiation using arrays of signaling mircoenvironments, Molecular Systems Biology (2006), Article No. 37, pp. 1-14, © 2006 EMBO and Nature Publishing Group.
Francesca Soncin et al., www.StemCells.com, Abrogation of E-Cadherin-Mediated Cell-Cell Contact in Mouse Embryonic Stem Cells Results in Reversible LIF-Independent Self-Renewal, Stem Cells 2009; 27: pp. 2069-2080.
Kenneth M. Yamada et al., Modeling Tissue Morphogenesis and Cancer in 3D, Leading Edge Review, Cell 130, Aug. 24, 2007, pp. 601-610, © 2007 Elsevier Inc.
Qi-Long Ying et al., BMP Induction of Id Proteins Suppresses Differentiation and Sustains Embryonic Stem Cell Self-Renewal in Collaboration with STAT3, Cell, vol. 115, Oct. 31, 2003, pp. 281-292, © 2003 by Cell Press.
Qi-Long Ying et al., http://www.nature.com/naturebiotechnology, Conversion of embryonic stem cells into neuroectodermal precursors in adherent monoculture, Published online Jan. 13, 2003, vol. 21, pp. 183-186.
Asad Raza et al., www.elsevier.com/locate/biomaterials, The influence of matrix properties on growth and morphogensis of human pancreatic ductal epithelial cells in 3D, Biomaterials, vol. 34, No. 21, Apr. 1, 2013, pp. 5117-5127, © 2013 Elsevier Ltd., See EP Search Report and International Search Report.
M.Ehrbar et al., Elucidating the Role of Matrix Stiffness in 3D Cell Migration and Remodeling, Biophysical Journal, Biophysical Society, US, vol. 100, No. 2, Nov. 16, 2011, pp. 284-293, © 2011 by the Biophysical Society, See EP Search Report & International Search Report.
Adrian Ranga et al., www.sciencedirect.com, High-throughput approaches for the analysis of extrinsic regulators of stem cell fate, Current Opinion in Cell Biology, vol. 24, No. 2, Apr. 1, 2012, pp. 236-244, © 2012 Elsevier Ltd., See EP Search Report & International Search Report.
Victoria Fox et al., www.StemCells.com, Cell-Cell Signaling Through NOTCH Regulates Human Embryonic Stem Cell Proliferation, Stem Cells 2008; 26: pp. 715-723, © AlphaMed Press.
Jayanta Debnath et al., www.sciencedirect.com, Morphogenesis and oncogenesis of MCF-10A mammary epithelial acini grown in three-dimensional basement membrane cultures, Methods 30 (2003) pp. 256-268, © 2003 Elsevier Science (USA).
Martin Ehrbar et al., Biomoleular Hydrogels Formed and Degraded via Site-Specific Enzymatic Reactions, Biomacromolecules 2007, 8, pp. 3000-3007, © 2007 American Chemical Society.
Adam J. Engler et al., Matrix Elasticity Directs Stem Cell Lineage Specification, Cell 126, Aug. 25, 2006, pp. 377-689, © 2006 Elsevier Inc.
Christopher J. Flaim et al., http:// www.nature.com/naturemethods, An extracellular matrix microarray for probing cellular differentiation, Nature Methods, vol. 2, No. 2, Feb. 2005, pp. 119-1125, © 2005 Nature Publishing Group.
P.M. Gilbert et al., www.sciencemag.org, Substrate Elasticity Regulates Skeletal Muscle Stem Cell Self-Renewal in Culture, Science, vol. 329, Aug. 27, 2010, pp. 1078-1082.
Elan Gin et al., www.elsevier.com/locate/yjtbi, A model for cyst lumen expansion and size regulation via fluid secretion, Journal of Theoretical Biology 264 (2010) pp. 1077-1088, © 2010 Elsevier Ltd.
Barbara González et al., www.StemCells.com, EpCAM Is Involved in Maintenance of the Murine Embryonic Stem Cell Phenotype, Stem Cells 2009; 27: pp. 1782-1791, © AlphaMed Press.
Samy Gobaa et al., Artificial niche microarrays for probing single stem cell fate in high throughput, Nature Methods, vol. 8, No. 11, Nov. 2011, pp. 949-957.
Linda G. Griffith et al., www.nature.com/reviews/molcellbio, Capturing complex 3D tissue physiology in vitro, Nature Reviews, Moleular Cell Biology, vol. 7, Mar. 2006, pp. 211-224.
Gabriel Helmlinger et al., http://www.nature.com/naturebiotechnology, Solid stress inhibits the growth of multicellular tumor spheroids, Nature Biotechnology, vol. 15, Aug. 1997, pp. 778-783 © 1997 Nature Publishing Group.
Liang Jin et al., www.pnas.org/cgi/doi/10.1073/pnas.1301889110, Colony-forming cells in the adult mouse pancreas are expandable in

(56) References Cited

OTHER PUBLICATIONS

Matrigel and form endocrine/acinar colonies in laminin hydrogel, PNAS, Mar. 5, 2013, vol. 110, No. 10, pp. 3907-3912.

Morteza Khalilian et al., http://rsif.royalsocietypublishing.org/, Estimating Young's modulus of zona pellucida by micropipette aspiration in combination with theoretical models of ovum, Journal of the Royal Society Interface, pp. 687-694, Published online Oct. 14, 2009, © 2009 The Royal Society.

Ferdous Khan et al., www.elsevier.com/locate/biomaterials, Strategies for cell manipulation and skeletal tissue engineering using high-throughput polymer blend formulation and microarray techniques, Biomaterials 31 (2010), pp. 2216-2228, © 2009 Elsevier Ltd.

Thomas P. Kraehenbuehl et al.,Three-dimensional biomaterials for the study of human pluripotent stem cells, Nature Methods, vol. 8, No. 9, Sep. 2011, pp. 731-736, © 2011 Nature America, Inc.

Mark A. Labarge et al., www.rsc.org/ibiology, Human mammary progenitor cell fate decisions are products of interactions with combinatorial microenvironments, Integrative Biology, 2009, 1, pp. 70-79, © The Royal Society of Chemistry.

Seung Tae Lee et al., www.elsevier.com/locate/biomaterials, Engineering integrin signaling for promoting embryonic stem cell self-renewal in a precisely defined niche, Biomaterials 31 (2010), pp. 1219-1226, © 2009 Elsevier Ltd.

Vivian S.W. Li et al., http://dx.doi.org/10.1053/j.gastro.2012.05.017, In Vitro Expansion and Transplantation of Intestinal Crypt Stem Cells, Imaging and Advanced Technology, Gastroenterology 2012;143: pp. 30-34, © 2012 by the AGA Institute.

M.P. Lutolf et al., Synthesis and Physicochemical Characterization of End-Linked Poly(ethylene glycol)-co-peptide Hydrogels Formed by Michael-Type Addition, Biomacromolecules 2003, 4, pp. 713-722, © 2003 American Chemical Society.

www.elsevier.com/locate/biomaterials, Leenaporn Jongpaiboonkit et al., "An adaptable hydrogel array format for 3-dimensional cell culture and analysis", Biomaterials, Elsevier Science Publishers BV., Barking, GB, vol. 29, No. 23, Aug. 1, 2008, pp. 3346-3356, XP022696727.

Derek M. Doroski, et al., "Cyclic Tensile Promotes Fibroblastic Differentiation of Marrow Stromal Cells Encapsulated in Poly(Ethylene Glycol)-Based Hydrogels", Tissue Engineering: Part A, vol. 16, No. 11, 2010, pp. 3457-3466.

Gonzalez-Tello, Pedro: et al; "Density and Viscosity of Concentrated Aqueous Solutions of Polyethylene Glycol" Journal of Chemical & Engineering Data, 39, 611-614, 1994.

Russian Official Action issued in corresponding Russian Patent Application No. 2015152344 dated Feb. 14, 2018.

European Office Action issued in corresponding European Patent Application No. 14 722 229.3 dated Jul. 19, 2018.

\* cited by examiner

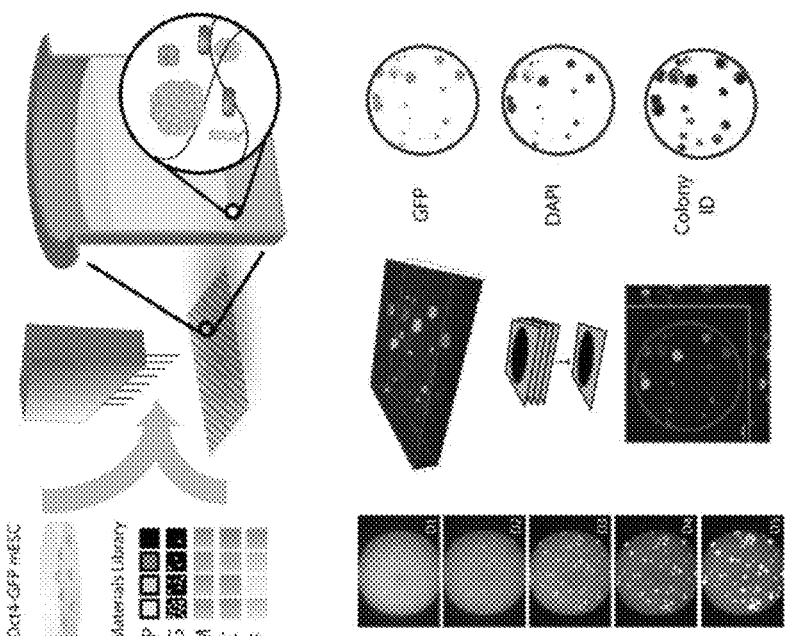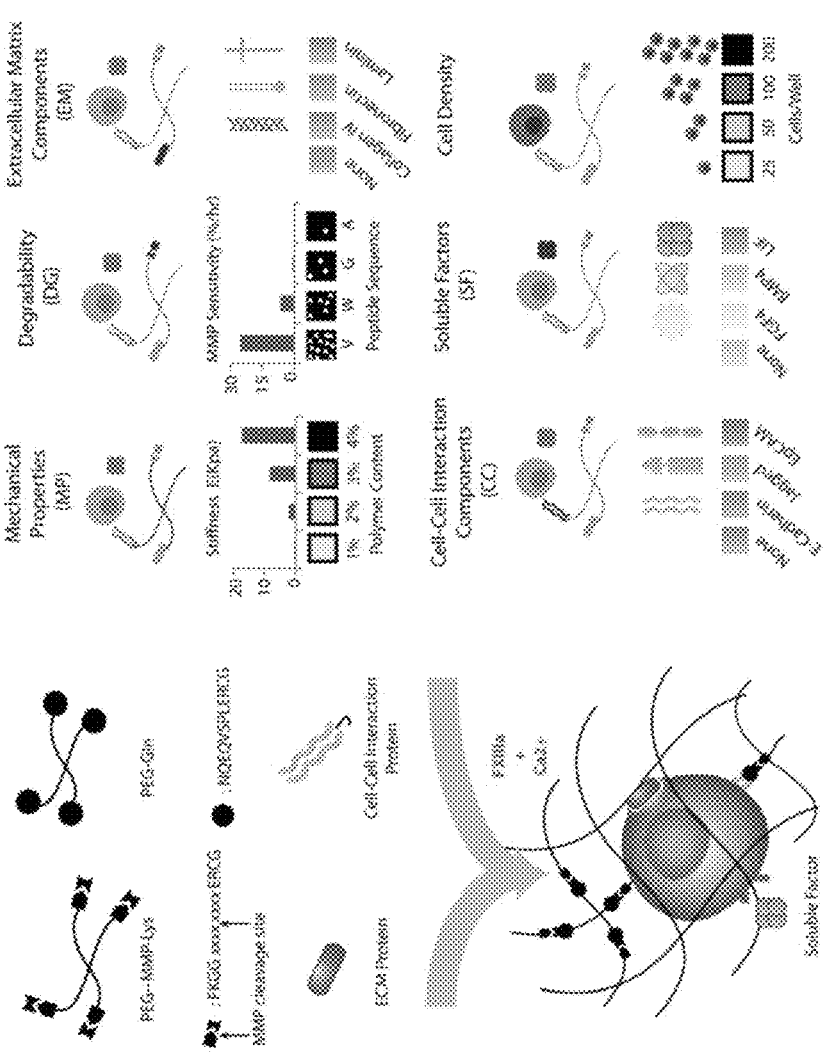

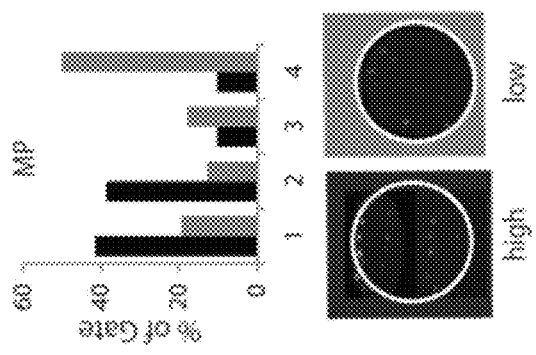
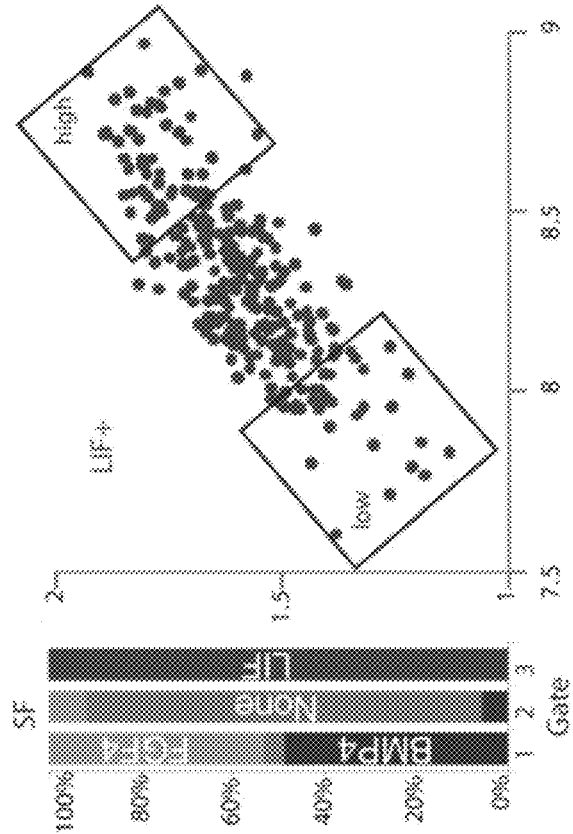
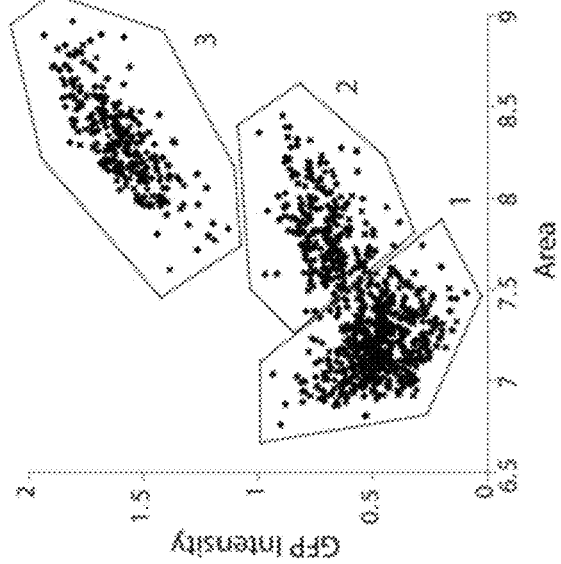
Fig. 2b
Fig. 2c
Fig. 2d

Fig. 3a
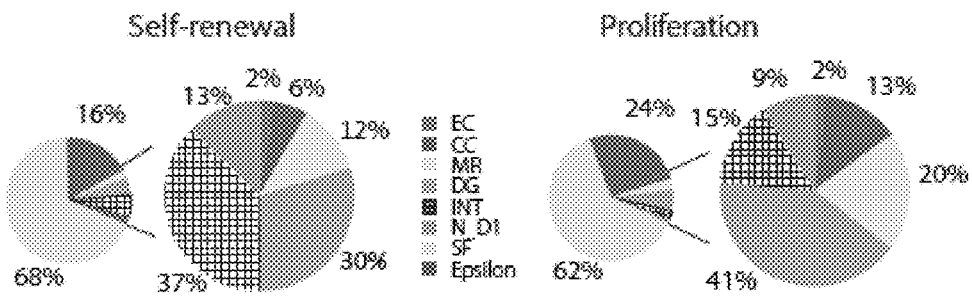
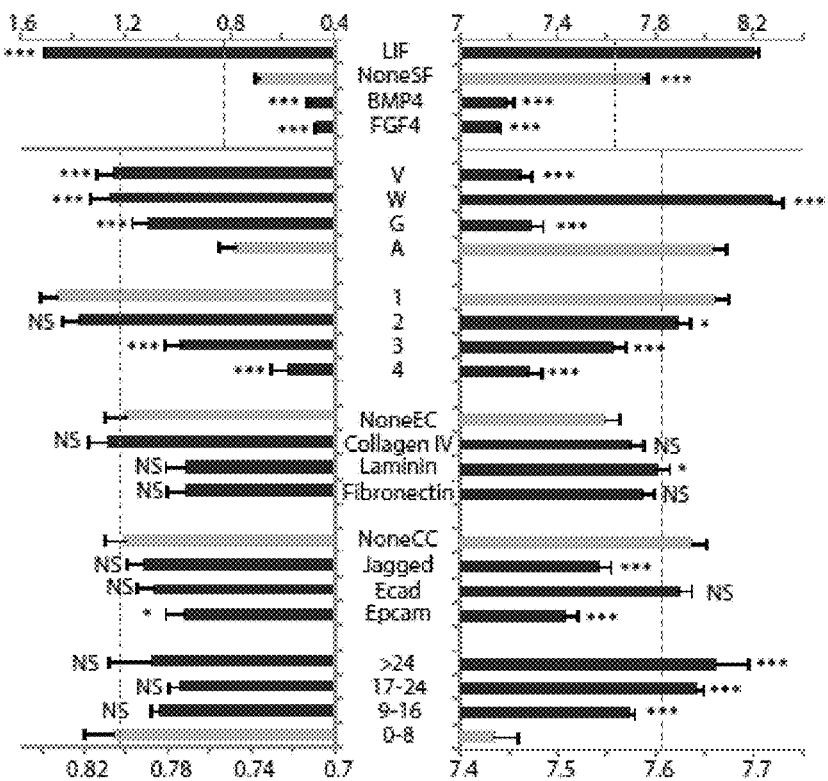
Fig. 3b
Fig. 3d
Fig. 3f
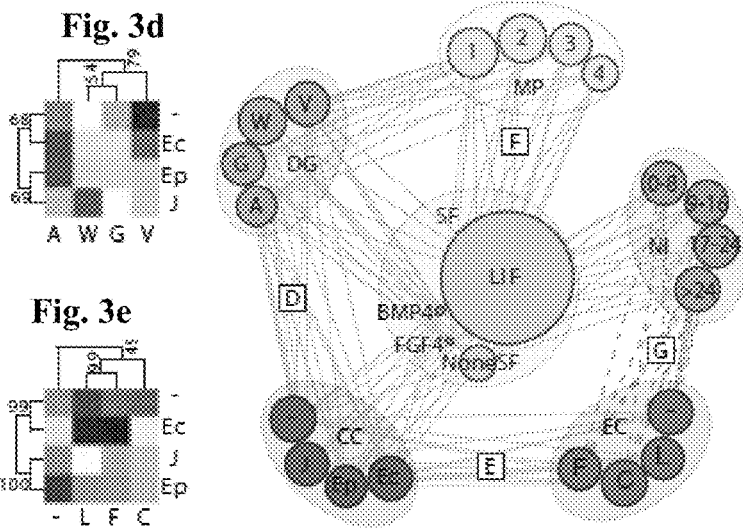
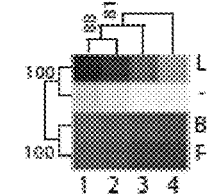
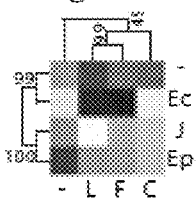
Fig. 3e
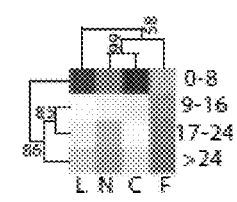
Fig. 3g
Fig. 3c

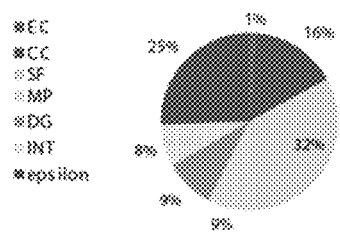
Fig. 5a
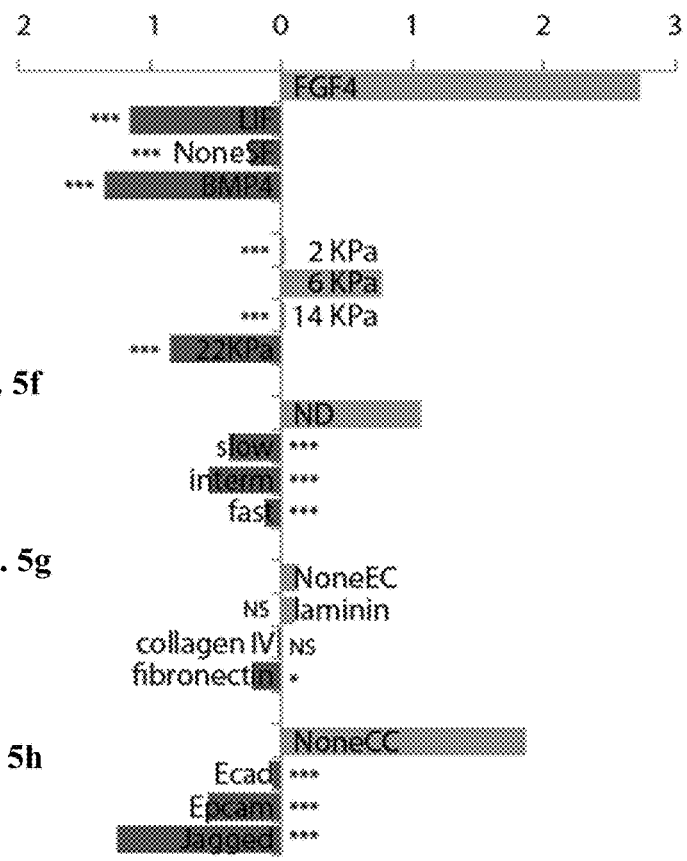
Fig. 5b
Fig. 5c
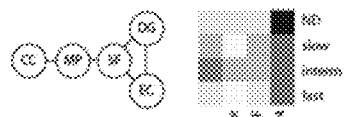
Fig. 5f
Fig. 5d
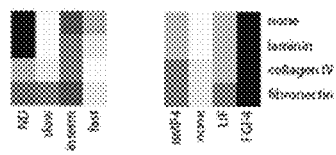
Fig. 5g
Fig. 5e
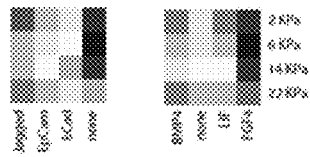
Fig. 5h

ARRAYS OF DISCRETE CELL CULTURE MICROENVIRONMENTS, METHODS OF MAKING SUCH ARRAYS AND USES THEREOF

The present invention pertains to arrays of discrete volumes of cell culture microenvironments possessing different properties, i.e. different mechanical and/or biochemical properties (i.e. cell adhesion, signalling, degradability) influencing cell phenotype and fate, i.e. proliferation/self-renewal, colony formation, differentiation and/or migration, methods of making such arrays, a kit-of-parts for making such arrays and a combinatorial method of testing the influence of hydrogel formulations on cell growth behaviour, in particular of difficult-to-culture cell types such as stem cells.

BACKGROUND OF THE INVENTION

Two-dimensional cell culture systems as well as naturally derived three-dimensional cell culture systems as models to elucidate complex cell behaviour, notably in the field of cancer or stem cell research, have been known for many years.

Two-dimensional cell culture systems have the drawback of not allowing for gene expression patterns and cellular phenotypes that closely resemble those found in vivo. Further, they cannot be expected to faithfully reproduce certain key physiological features of the in vivo cell culture microenvironment, notably spatial constraints, proteolytic remodeling, stiffness-mediated mechanotransduction and appropriate mode of presentation of ligands.

Naturally derived 3D cell culture systems have poorly defined compositions and show batch to batch variation, which makes it impossible to alter their properties in systematic ways and to independently control their key matrix parameters.

Accordingly, it is an object of the present invention to overcome the drawbacks of the prior art, in particular to provide tools and methods that enable rapid identification of cell culture cell culture microenvironments controlling desired cell behaviours.

SUMMARY OF THE INVENTION

A first aspect of the invention pertains to an array of discrete volumes of cell culture microenvironments (preferably each) possessing different properties influencing the behaviour of encapsulated cells.

As understood herein, the term "encapsulated in a cell culture microenvironment" or similar expressions mean that the cell(s) is/are embedded in a matrix in such a way that they are completely surrounded by said matrix, thereby mimicking naturally occurring cell growth conditions.

As understood herein, the term "microenvironment" or "volume of microenvironment", respectively, means a volume that is suitable for high-throughput testing appliances, in particular multi well plates. Typical volumes being analyzed in multi well plates are in the range of about 100 nl to about 500 μl, preferably of about 200 nl to about 20 μl.

The term "discrete volumes" relates to spatially separated spots or areas within the array. The separated spots or areas may be in contact with each other or separated from each other by e.g. a plastic barrier. Into or onto each of these discrete volumes, cells of a desired cell type can be placed in such a way that they are separated from each other. They do not come into contact with each other from the beginning of an experiment and remain so over time, thereby growing independent from a neighbouring volume and only under the influence of their cell culture microenvironment.

In particular, an array of three-dimensional hydrogels having discrete volumes and possessing different properties influencing cell proliferation/self-renewal, colony formation, differentiation and/or migration may be used. The hydrogels used, which are obtained by cross-linking hydrogel precursor molecules, are preferably hydrophilic polymers such as poly(ethylene glycol) (PEG)-based polymers, most preferably multiarm PEG-based polymers that are crosslinked by cell-compatible crosslinking reactions.

As understood herein, "crosslinkable by cell-compatible reaction(s)" (or similar terminology), comprises reactions both on the basis of (i) covalent bond formation, chosen from the group consisting of a) enzymatically catalyzed reactions, preferably depending on activated transglutaminase factor XIIIa; and b) not-enzymatically catalyzed, and/or uncatalyzed reactions, preferably a Michael addition reaction; and/or ii) non-covalent bond formation (e.g. on the basis of hydrophobic interactions, H-bonds, van-der-Waals or electrostatic interactions; in particular induced by temperature changes or changes in ionic strength of a buffer).

In preferred embodiments, PEG-based precursor molecules are chosen such as to be cross-linkable using either thrombin-activated Factor XIIIa under physiological conditions by a crosslinking mechanism that is detailed in Ehrbar et al., 2007, or via mild chemical reactions by a crosslinking mechanism as detailed in Lutolf et al., 2003.

Cross-linking of the hydrogel precursor molecules is done in the presence of cell types to be studied in discrete volumes of the array, in such a way that the cells are encapsulated by the hydrogel matrix, i.e. are residing in a distinct cell culture microenvironment.

Various mechanical and biochemical factors from the cell culture microenvironment influence the behaviour of cells in terms of proliferation/self-renewal, differentiation, migration and/or colony formation in 3D. In an array according to the invention, these factors can differ from volume to volume and thus allow the influence of individual factors or combinations of factors on a cell type to be studied simultaneously in a multitude, preferably hundreds or thousands of unique cell culture microenvironments. Thus, the role of individual factors on cell fate in cell culture microenvironments can be systematically dissected and in particular hydrogel cell culture microenvironments controlling the behaviour of difficult-to-culture cell types such as stem cells may be rapidly identified.

Mechanical properties of the three-dimensional hydrogel matrix according to the invention can be changed by varying the polymer content of the cell culture microenvironments, as well as the molecular weight and/or functionality (number of sites available for crosslinking) of the polymeric gel precursors. Thus, e.g. the stiffness of the matrix, represented by Young's moduli (E), can vary between 300 to 5400 Pa.

Further, physicochemical properties of the matrix over time can be changed by conferring degradation characteristics to the gel matrix via incorporation into the matrix of peptides of different sensitivities (i.e. $k_{cat}/K_m$) to cell-secreted proteases such as matrix-metalloproteinases (MMPs) or plasmin. Susceptibility to proteases and the resulting change in physicochemical properties of the matrix when proteases are secreted by the cells allows for efficient cell proliferation and migration in the three-dimensional matrix. To match the mechanical properties of hydrogel matrices having different susceptibilities to proteolytic degradation, the precursor content of the matrix can be fine-tuned by varying the polymer precursor content of the matrix, the molecular weight and/or functionality (number of sites available for crosslinking) of the polymeric gel precursors. In a PEG-based hydrogel matrix, susceptibility to proteases can be changed e.g. by incorporating different peptide sequences with different sensitivities to cell-secreted proteases into the matrix precursor molecules, as is outlined in more detail below.

Biochemical properties of cell culture microenvironments can be modulated by addition of one or more biologically active molecules to the matrix. As used herein, these biologically active molecules may be selected e.g. from the group of
  i) extracellular matrix-derived (ECM) factors;
  ii) cell-cell interaction factors; and/or
  iii) cell signalling factors.

The extracellular matrix-derived factors i) used may be, for instance, ECM proteins such as laminins, collagens, elastins, fibronectin or elastin, proteoglycans such as heparin sulfates or chondroitin sulfates, non-proteoglycan polysaccharides such as hyaluronic acids, or matricellular proteins seen as those of the CN family of proteins, fibulins, osteopontin, periostin, SPARC family members, tenascins, or thrombospondins. These ECM factors can either be used in a full-length version or as smaller, functional building blocks such as peptides and oligosaccharides.

The cell-cell interaction proteins ii), mostly transmembrane proteins, used may be proteins involved in cell-cell adhesion such as cadherins, selectins or cell adhesion molecules (CAMs) belonging to the Ig superfamily (ICAMs and VCAMs) or components of transmembrane cell signaling system such as Notch ligands Delta-like and Jagged.

The cell signaling factors iii) used may be growth factors or developmental morphogens such as those of the following families: adrenomedullin (AM), angiopoietin (Ang), autocrine motility factor, bone morphogenetic proteins (BMPs), brain-derived neurotrophic factor (BDNF), epidermal growth factor (EGF), Erythropoietin (EPO), fibroblast growth factor (FGF), glial cell line-derived neurotrophic factor (GDNF), granulocyte colony-stimulating factor (G-CSF), granulocyte macrophage, colony-stimulating factor (GM-CSF), growth differentiation factor-9 (GDF9), hepatocyte growth factor (HGF), hepatoma-derived growth factor (HDGF), insulin-like growth factor (IGF), leukaemia inhibitory factor (LIF), migration-stimulating factor, myostatin (GDF-8), nerve growth factor (NGF) and other neurotrophins, platelet-derived growth factor (PDGF), Thrombopoietin (TPO), transforming growth factor alpha (TGF-α), transforming growth factor beta (TGF-β) tumor_necrosis_factor-alpha (THF-α), vascular endothelial growth factor (VEGF), Wnt signaling pathway, placental growth factor (PlGF), or members of the large class of cytokines or chemokines.

Extracellular matrix-derived i) and cell-cell interaction factors ii) can be site-specifically attached to the hydrogel matrix either before or during cross-linking. Gel functionalization with biologically active molecules can be achieved by direct covalent bond formation between free functional groups on the biomolecule (e.g. amine or thiol groups) or a peptidic substrate for a crosslinking enzyme (e.g. a transglutaminase) and the gel network, or via affinity binding between a domain on a chimeric/tagged protein and an auxiliary protein attached to the gel. The tagged proteins include those having Fc-tags, biotin-tags or His-tags such as to enable binding to ProteinA (or ProteinG, ProteinA/G), Streptavidin (or NeutrAvidin) or NTA.

The biomolecules may require different gel-tethering strategies to the hydrogel networks. Larger ECM-derived or ECM-mimetic proteins and peptides are preferably attached to the hydrogel by non-specific tethering using linear, heterodifunctional linkers. One functional group of this linker is reactive to the functional groups attached to termini of the polymer chains, preferably thiols. The other functional group of the linker is capable of non-specifically tethering to the biomolecule of interest via its amine groups. The latter functional group is selected from the group consisting of succinimidyl active ester such as N-hydroxysuccinimide (NHS), succinimidyl alpha-methylbutanoate, succinimidyl propionate; aldehyde; thiol; thiol-selective group such as acrylate, maleimide or vinylsulfone; pyridylthioesters and pyridyldisulfide. Preferably NHS-PEG-maleimide linkers are attached to the biomolecules.

The cell signaling factors iii) can either be added to the cross-linked hydrogel matrix encapsulating cells in a soluble form in spatially separate areas and thus are allowed to diffuse freely into the matrix to reach the cells. Alternatively, they can be tethered to the matrix in the same way as described above for extracellular matrix-derived i) and cell-cell interaction factors ii).

Another aspect of the present invention pertains to a method of making arrays as outlined herein. In particular, this method comprises the steps of
a) providing one or more different hydrogel precursor molecules;
b) combining and dispensing different combinations of hydrogel precursor molecules according to step a) onto or into discrete volumes of a substrate, preferably a multi-well plate;
c) adding to said discrete volumes one or more biologically active molecules and either attaching said molecules to at least one of the hydrogel precursor molecules present or the hydrogel formed in step e) or allowing them to diffuse freely;
d) adding cells onto/into said discrete volumes of the substrate; and
e) crosslinking said hydrogel precursor molecules to form a hydrogel matrix.

In step a) of the above described method the hydrogel precursor molecules used are preferably chemically or enzymatically reactive polymeric PEG-based precursor to which biomolecules can be tethered and that can be crosslinked by mechanisms that do not compromise cell viability. If the PEG-based precursors comprise (glutamine- and lysine-bearing) peptidic substrates for a transglutaminase such as e.g. factor XIIIa, crosslinking can be carried out by means of a this enzyme. Most preferably, the precursor molecules also comprise different proteolytically sensitive peptide sequences in order to allow for cell-mediated hydrogel degradation, i.e. localized changes in structural and mechanical properties of the matrix over time.

Step b) of the above described method is preferably carried out using an automated method for gel fabrication and miniaturized samples in order to achieve the required level of diversity in formulating 3D cell-containing matrices having large numbers of different cell culture microenvironments and to also achieve the required repetitions. To this end, a commercially available liquid handling robot is preferably used to accurately synthesize volumes as low as 100 to 500 nanoliters of each of the unique mixture of precursor molecules according to step a) preferably in triplicate, in a completely automated manner, onto a substrate, such as a glass slide or, preferably, into a multi-well plate such as a standard 1536-well plate. The latter format is preferred as it presents an ideal surface to volume ratio for the selected hydrogel drops and represents a standard format which can be adapted to various experimental setups. Once the 3D hydrogel matrix is generated, the system can function as a multimodal assay platform, where multiple readouts can be obtained in parallel.

In step c) of the above described method, the biologically active molecules are selected as outlined hereinbefore.

In step e) the cross-linking of the hydrogel precursor molecules to form a three-dimensional hydrogel matrix can be achieved by using at least one cross-linking agent. When PEG-based precursor molecules are used, thrombin-activated Factor XIIIa or a chemically reactive bi-functional oligopeptide bearing an MMP-sensitive substrate (as detailed in Lutolf et al., 2003) is the chosen cross-linking agent. However, it is also conceivable that the crosslinking may occur immediately upon combination of two different precursor molecules which are readily reactive towards each other (such as e.g. by highly selective so-called click chemistry or other chemical, not enzymatically catalyzed reaction such as e.g. of the Michael-type addition reaction).

The array of dispensed hydrogel precursors can be stored and used (i.e. brought in contact with cells for screening experiments) at a later time point. Storage is preferably conducted in a multi well plate (e.g. 96-, 384- or 1536-well plate) and can either be done using precursors in solution (with yet a cross-linking agent missing) or else lyophilized precursors, i.e. a powder. The powder is and remains unreacted, meaning that almost none of the structural component (e.g. PEG) of the precursor has reacted with the crosslinking agent. Upon e.g. addition of a buffer, the lyophilized precursors are solubilised and may then react with each other.

Yet another aspect of the present invention pertains to a combinatorial method of testing the influence of hydrogel. formulations on cell growth behaviour. In particular, this combinatorial method comprises the steps of
a) providing one or more different hydrogel precursor molecules;
b) combining and dispensing different combinations of hydrogel precursor molecules according to step a) onto/into discrete volumes of a substrate, preferably a multi-well plate;
c) further adding to said discrete volumes of said substrate one or more biologically active molecules and either attaching said molecules to at least one of the hydrogel precursor molecules present, or the hydrogel formed in step e) or allowing them to diffuse freely;
d) adding cells (of a desired cell type) onto/into said discrete volumes of the substrate;
e) crosslinking said hydrogel precursor molecules to form a hydrogel matrix;
f) allowing said cells to grow (and change their behaviour) in said discrete volumes of said hydrogel matrix;
g) monitoring said cells during step f) over time;
h) determining the behaviour for different cell culture microenvironments, wherein the behaviour is preferably chosen from the group consisting of the extent of proliferation, colony formation, differentiation, migration, or combinations thereof, preferably for the entire array of different cell culture microenvironments;
i) optionally, determining the synergistic and/or antagonistic effects on each other of the biologically active molecules and/or of the mechanical properties and/or susceptibilities to enzymatic degradation of the discrete cell culture microenvironments, preferably by proteinases;
j) optionally, identifying a specific hydrogel formulation, or range of hydrogel formulations, that instructs a certain cell behaviour;
k) optionally, isolating cells from at least one hydrogel cell culture microenvironments for further analysis, preferably a phenotypic assay, or for continuous cell culture or passaging.

The different hydrogel precursor molecules used in step a) are preferably selected as outlined elsewhere herein.

Step b) of the above described combinatorial method is preferably carried out using an automated method for as outlined elsewhere herein.

In step c) of the above described combinatorial method, the biologically active molecules referred to may be selected as outlined elsewhere herein.

In step e), the cross-linking of the hydrogel precursor molecules provided in step a) can be achieved as described elsewhere herein.

In the combinatorial method step f), the cells are allowed to proliferate/self-renew, form colonies, differentiate or migrate in discrete volumes of the hydrogel matrix, preferably for several days up to weeks.

Monitoring of cell behaviour in combinatorial method step g) may occur at fixed time intervals, e.g. after a certain number of days, and repeatedly. Monitoring is carried out, for instance, using automated imaging techniques, either conventional or confocal microscopy, and can include time-lapse imaging.

Determination of proliferation/self-renewal, colony formation, differentiation, and/or migration behaviour for different cell culture microenvironments in combinatorial method step h) can, for instance, be done using wide-field microscopy or with cells expressing fluorescent markers such as green fluorescent protein (GFP) or immunostaining cells using fluorescent antibodies and quantifying the fluorescence intensities as they grow and change their behaviour by e.g. self-renewing or differentiating or by quantifying the development of single cells into multicellular colonies in 3D using microscopy. Thus, for instance read-outs of the number and kinetics of cells growing in each discrete cell culture microenvironment, the level of reporter gene expression, or the three-dimensional morphology of growing cells and cell colonies can be obtained. Other morphometric measurements such as, for instance, cell or colony eccentricity, solidity, degree of polarity, can be assessed and quantified. The variability of these measures can also be quantified to assess a measure of heterogeneity.

The quantification of cell behaviour of the entire array of diverse cell culture microenvironments in combinatorial method step i) may yield one or more hydrogel formulations that can be further used and up-scaled for 3D cell culture in desired applications.

In step j), if required, specific cell culture microenvironments can be digested to harvest cells. The harvesting of cells is useful for for continuous cell culture/passaging as well as for downstream phenotypic assays, such as flow cytometry, gene expression analyses, in vivo assays, etc.

Yet another aspect of the invention pertains to a kit-of-parts for making and optionally using 3D hydrogel microarrays as outlined hereinbefore and which is suitable in the combinatorial method as outlined hereinbefore. Such a kit comprises as separate components
a) one or more hydrogel precursor molecules, preferably one or more multiarm PEG molecules (as outlined elsewhere herein);
b) one or more biologically active molecules (as outlined elsewhere herein);

c) optionally, at least one crosslinking agent for the precursor molecules a) (as outlined elsewhere herein); and d) instructions for use of said components, preferably in accordance with the methods outlined hereinbefore.

The instructions for use d) of components a) to c) within the kit-of-parts are packaged together with said components and provide instructions in accordance with the method of making a three-dimensional matrix as well as a the combinatorial method of studying the influence of hydrogel cell culture microenvironments on cell proliferation and/or differentiation as described above.

In sum, the inventors had to face various challenges during the course of the invention, and the most promising possibilities to appropriately overcome such obstacles were not readily predictable:

1. Requirements Related to Liquid Hydrogel Precursor Characteristics and Preparation 1.1 To enable high-throughput routines, hydrogel precursors should be compatible with automatic liquid handling robotics. To be reproducibly dispensed they should neither be too viscous nor too sticky. It has been found that liquids ranging in viscosities from that of water to that of 10% (w) aqueous solution of PEG with a molecular weight between 10 and 40 kDa can be used for reliable dispensing. Most precursors of naturally derived hydrogel networks based on proteins or sugars (e.g. Matrigel™, collagen, fibrin, laminin, hyaluronic acid etc., i.e. the state-of-the-art and most commonly used gels for 3D cell culture) cannot be reliably dispensed because they do not fulfill this requirement. These most commonly used gel formulations could not be used to reduce the concept to practice.

The aforementioned viscosity range can e.g. be achieved by using hydrogel backbones that are not based on proteins or sugars but rather hydrophilic polymers, most preferably branched poly(ethylene glycol) molecules having between 3 and 8 arms with a molecular weight between 2000 and 5000 kDa, that are formed at a precursor concentration range between 1 and 10% (w/v).

1.2 The hydrogel precursors should be stable and not gel spontaneously at room temperature or spontaneously react upon exposure to light. Most precursors of naturally derived hydrogel networks (e.g. Matrigel™, collagen, fibrin) spontaneously gel at room temperature or even lower temperatures. In addition, many precursors of synthetic hydrogels (e.g. photopolymerized PEG gels) are light-sensitive and thus spontaneously form gel. These most commonly used gel formulations are not ideal to reduce the concept to practice.

To prevent spontaneous gelling, crosslinking reactions can be used that are based on enzymatic reactions, preferably those based on transglutamainases, in which case the active enzyme can be either added at the very last step of the microarray production (i.e. after conduction of combinatorial mixing), or in a solution that is deprived of Calcium which is essential for the activity of the crosslinking enzyme, or by cooling down the plate below circa 0° Celsius to dramatically slow down the enzymatic crosslinking reaction.

1.3 There should be a controllable triggering event for the initiation of gelation of the liquid precursors. Specifically, mixing of components before addition of this gelation-triggering component should be non-reactive. This is not the case for naturally derived hydrogel networks and these formulations are therefore not ideal to reduce the concept to practice.

The aforementioned triggering event can e.g. be the addition of an enzyme that induces crosslinking, preferably an enzyme that is a member of the transglutaminase family, the addition of Calcium to a solution which is calcium-deprived such that the enzyme is inactive, or by heating up the plate to room temperature from circa 10° Celsius to trigger the enzymatic crosslinking reaction.

1.4 There should be a defined period between activation of the liquid precursor, when the material must be freely and controllably manipulated in liquid form, before solidification into hydrogel form. Specifically, the material is to be handled in liquid form at room temperature and should not gel for a minimum time period of 2 to 4 minutes which is the typical time required for dispensing onto the final plate. In the most commonly used gel formulations for 3D cell culture, polymerization kinetics are uncontrollable and such a set time period does not exist. These formulations were therefore not ideal to reduce the concept to practice. In the context of the present invention, this problem is preferably overcome by triggering gelation by a crosslinking enzyme, which is additionally temperature-sensitive (i.e., can be deactivated by temperature decrease), providing a powerful means to tune the length of the time period before viscosity becomes too high for successful dispensing. Most suitable enzymes for use in the context of the present invention are members of the family of transglutaminases, most preferably thrombin-activated Factor XIIIa.

2. Requirements Related to Solid Hydrogel Properties 2.1 The final gel material should be non-swelling and non-shrinking. Swelling or shrinking is defined here as the increase or decrease in volume between the volume of the precursor solution (that is dispensed into the plate) and the hydrogel after it has reached an equilibrium with the medium in which it is placed. Specifically, the swelling ratio, defined here as the final volume of the gel in equilibrium with water divided by the volume of the gel just after synthesis (i.e. corresponding to the volume of the precursor solution), should be between 80 and 130%. Notably, hydrogel swelling in water is typically measured as follows: Gels are synthesized (typically 25 μL in volume), weighed in air and ethanol before and after swelling tor 48 h in 1 mL of deionized water and after freeze-drying, using a density determination kit. On the basis of Archimedes' buoyancy principal, the gel volumes after cross-linking ($V_{g,c}$) and after swelling ($V_{g,s}$) are determined. The ratio between $V_{g,s}/V_{g,c}$ is defined as the swelling ratio. Lack of this requirement may lead to inhomogeneous material properties, material deformation and potential gel detachment from substrate, each of which is detrimental for reducing this concept to practice. To the best of the inventors' knowledge, most if not all synthetic hydrogel systems extensively swell after cross-linking and could thus not ideally be used to reduce this concept to practice. The inventors have engineered polymer precursor architectures (i.e. functionality and molecular weights) in order to in order to identify gels that are non-swelling and non-shrinking. Specifically, hydrogels formed from branched hydrophilic polymers, most preferably poly(ethylene glycol) macromers having 8 arms (i.e. 8 functionalities) with a molecular weight of 5000 kDa each and bearing peptidic substrates for transglutaminase crosslinking enzymes, when formed at a precursor concentration range between 1 and 10% (w/v) have been identified by the inventors (from a large library of other macromer architectures and crosslinking reactions) to fulfil this non-swelling and non-shrinking criteria.

2.2 The final gel material should have biophysical properties (i.e. stiffness) that are independently controllable from its biochemical properties (i.e. degradability and signaling). Specifically, altering gel properties by changing polymer content should not change the degradability. The most commonly used gels for 3D cell culture (e.g. Matrigel™, collagen, fibrin, laminin) do not allow to change the gels biophysical properties independently from its biochemical properties and could thus not ideally be used to reduce this concept to practice. The inventors solved this problem by engineering hydrogel systems in which changes in stiffness are linearly dependent on changes in polymer content. When changing the degradability of gels via incorporation of different protease substrate in the gel backbone, this linearity allows for precisely matching the biophysical properties of gels having different degradabilities.

2.3 The final gel material should degrade by highly localized breaking down of the gel backbone (i.e. where holes are created within the gels) rather than global, non-specific degradation (i.e. where the entire gel piece dissolves). Many commonly used synthetic hydrogel materials such as those comprising hydrolytically unstable ester bonds (e.g. PEG gels formed via acrylate groups) degrade by non-localized mechanisms. Moreover, many commonly used gels for 3D cell culture (e.g. Matrigel™ or fibrin) dissolve globally and non-specifically (Matrigel™ is especially prone to uncontrollable degradation) and could thus not ideally be used to reduce this concept to practice. In the context of the present invention, highly localized breakdown of the gel backbone is achieved by placing a protease substrate, attached to the termini of the branched hydrophilic polymers, in the backbone of the hydrogel network such that cell-secreted proteases anchored to the cell membrane (e.g. membrane bound proteases) cleave the hydrogels just in close proximity to the cell surface and not beyond. Preferably, such gels are rendered degradable by matrix metalloproteinases (MMP) via the incorporation of peptides of different sensitivities (i.e. $k_{cat}/K_m$) to cell-secreted MMPs.

2.4 The final gel material should allow for biochemical factors (e.g. proteins or peptides) to be attached to it without reducing their bioactivity upon attachment. Moreover, the attachment of biochemical factors must not affect biophysical gel properties. Many commonly used synthetic hydrogel materials are formed via crosslinking chemistries that are either incompatible with functional incorporation of biochemical factors or alter their biophysical characteristics upon factor incorporation; these systems could thus not ideally be used to reduce this concept to practice. Moreover, the most commonly used gels for 3D cell culture (e.g. Matrigel™, collagen, fibrin, laminin) do not allow to specifically incorporate biochemical factors and could thus not ideally be used to reduce this concept to practice. The inventors have engineered synthetic hydrogel systems that allow attaching up to 1 mg/ml of protein or 1 mM of peptide without altering the stiffness of the final gel by more than 20%.

This is achieved preferably by site-specifically attaching biochemical factors to the hydrogel matrix either before or during crosslinking. Gel functionalization with biologically active molecules can be achieved by direct covalent bond formation between free functional groups on the biomolecule (e.g. amine or thiol groups) or a peptidic substrate for a crosslinking enzyme (e.g. a transglutaminase) and the gel network, or, preferably in the case of sensitive cell-signaling proteins, via affinity binding between a domain on a chimeric/tagged protein and an auxiliary protein attached to the gel. The tagged proteins include those having Fc-tags, biotin-tags or His-tags such as to enable binding to ProteinA (or ProteinG, ProteinA/G), Streptavidin (or NeutrAvidin) or NTA. The biomolecules may require different gel-tethering strategies to the hydrogel networks. Larger ECM-derived or ECM-mimetic proteins and peptides are preferably attached to the hydrogel by non-specific tethering using linear, heterodifunctional linkers. One functional group of this linker is reactive to the functional groups attached to termini of the polymer chains, preferably thiols. The other functional group of the linker is capable of non-specifically tethering to the biomolecule of interest via its amine groups. The latter functional group is selected from the group consisting of succinimidyl active ester such as N-hydroxysuccinimide (NHS), succinimidyl alphamethylbutanoate, succinimidyl propionate; aldehyde; thiol; thiol-selective group such as acrylate, maleimide or vinylsulfone; pyridylthioesters and pyridyldisulfide. Preferably NHS-PEG-maleimide linkers are attached to the biomolecules.

2.5 The final gel material should adhere to the microarray substrate which is typically plastic or glass. Specifically, this substrate is treated or untreated glass microscope slides, standard tissue-culture treated or non-treated gamma-irradiated cell culture plastic labware, treated or untreated well plates, treated or untreated high density (384, 1536 well) cell culture plates. Lack of this requirement may lead to gel detachment and loss of test sample. Many commonly used synthetic hydrogel materials are not adherent to such surfaces and could thus not be used to reduce this concept to practice.

It has been found that hydrogel materials that do not swell or shrink possess the preferred adherence to the substrates as outlined above. Specifically, hydrogels formed from branched hydrophilic polymers, most preferably poly(ethylene glycol) macromers having 8 arms (i.e. 8 functionalities) with 3 molecular weight 5000 kDa each and bearing peptidic substrates for transglutaminase crosslinking enzymes, when formed at a precursor concentration range between 1 and 10% (w/v) have been identified by the inventors (from a large library of other macromer architectures and crosslinking reactions) to fulfil this non-swelling and non-shrinking criteria.

3. Requirements Related to Nano/Micro-Liter-Scale Robotic Dispensing 3.1. The robotic liquid handling apparatus should have the ability to precisely mix large liquid volumes, as well as to dispense nanoliter-range liquid drops in a spatially addressable format. Most commercially available liquid handling machines do not allow to dispense with nanoliter-range precision. Additionally, the liquid handling apparatus should maintain precision for liquids of widely differing viscosities. Specifically, accurate volumes should be maintained for liquids ranging in viscosities from that of water to 10% PEG. A commercially available liquid handling robot is preferably used to accurately dispense volumes as low as 50 nanoliters (max. +/−1% error in precision).

3.2 Strategies to avoid gel evaporation in micro- and especially the nano-liter volume range should be developed, requiring very tedious optimization work and protocol development. Specifically, evaporation should be avoided during the time between dispensing and medium addition on gelled samples. Specifically, evaporation of small volumes of precursor/gel (circa 100 nl-1 uL) should be avoided for approximately 20 minutes. Specifically, mixing and dispensing should be performed in controlled temperature and humidity, specifically, e.g. 25° C. and 30% relative humidity, from which a dew point temperature of e.g. 6° C. is calculated and set for the cooling block. Specifically, temperature of the substrate (typically multi-well plate) should be controlled by use of a cooling block. Specifically, ambient temperature and ambient relative humidity are used to calculate dew point, and cooling block is set at dew point. Specifically, the plate should be maintained at dew point while multiple dispense steps are performed. Specifically, after all gel dispense steps are performed, the plate should be placed upside in an incubator (37° C., 5% $CO_2$) for 20 minutes to allow complete gelation while preventing evaporation. Specifically, after gelation is complete, the plate should be quickly (circa 1 min) filled with a small amount of baseline medium (typically 1 μL in case of a 1536 well plate). Additionally, during the course of the assay, medium must be quickly exchanged. Specifically, medium can be spun out of the plate by centrifugation (circa 200-300 g).

3.3 Gel precursor liquid mixing should be performed in a precisely defined, hierarchically ordered sequence, requiring some tedious optimization work and protocol development. This requires extensive planning and optimization work. Specifically, differentially protease-sensitive polymer precursor stock solutions should first be diluted to different concentrations. Biochemical factors such as proteins and peptides should then be added to the solution, followed by cells and the cross-linking inducers which is preferentially a crosslinking enzyme. Failure to follow this sequence may lead to loss of independence between the various physical and chemical properties and failure to reduce the concept to practice. Incorrect sequence can also lead to incorrect concentrations of proteins, incorrect cell density or premature gelation.

3.4 Cell density and homogenous 3D distribution within the gel should be ensured, requiring some tedious optimization work and protocol development. Specifically, dispensing times and delay with respect to addition of cross-linker should be optimized. Additionally, gel volume should be optimized for specific substrate formats to ensure optimal cell viability (limited by diffusion) and evaporation prevention while maintaining miniaturized minimal volume. Specifically, gel volume is typically 1 μl for a well of a 1536 well plate, resulting in a gel height of approximately 500 μm.

BRIEF DESCRIPTION OF THE DRAWINGS

FIG. 1a: Crosslinking of the multiarm PEG-based pre-polymers under physiological conditions.

FIG. 1b: Influence on the mechanical properties (MP), Degradability (DG), Extracellular Matrix Components (EM), Cell-Cell Interaction Components (CC), Soluble Factors (SF).

FIG. 1c: Four levels of modulation for each of the five categories presented in FIG. 2.

FIG. 1d: Cell fat analysis.

FIG. 2b: All cell culture microenvironments plotted as colony area vs. GFP intensity.

FIG. 2c-d: Self-renewing and proliferating matrix characteristics in dependency of the matrix stiffness.

FIG. 3a-g: Systematic quantification on self-renewal and proliferation variation in dependency of the signalling cell culture microenvironment.

FIG. 5a-h: Systemic cell culture microenvironment factor analysis on factors modulating early neutral development.

DETAILED DESCRIPTION OF THE INVENTION

Figure 2A:
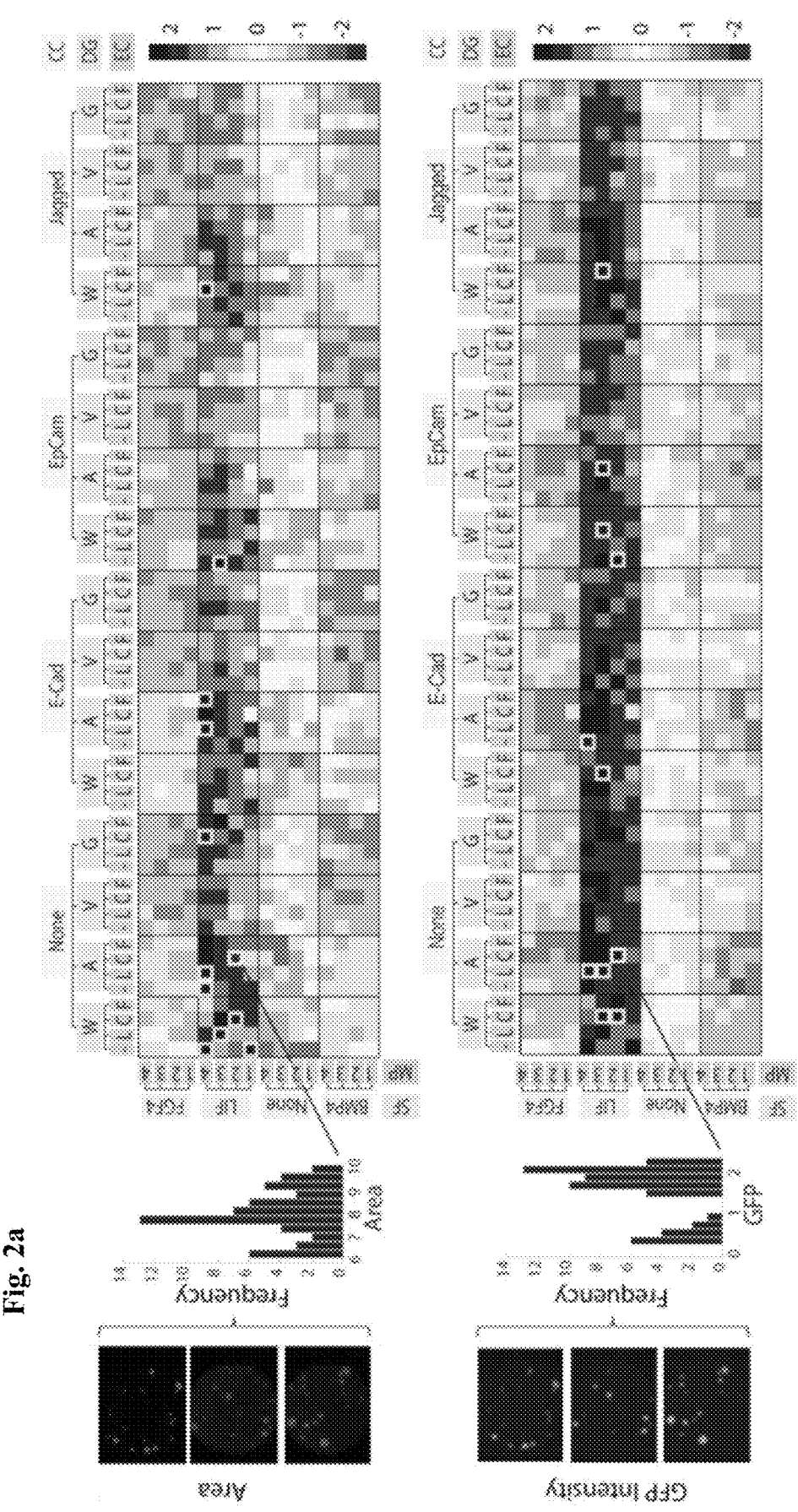
FIG. 2a: Heat Map representation for the combination of matrix effectors.
Figure 4A:
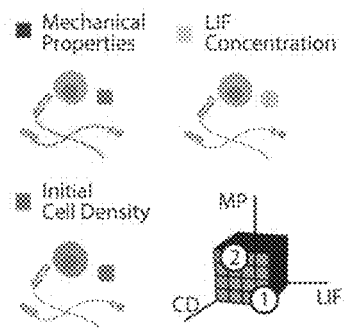
FIG. 4a-h: complementary assays on the effect of stiffness on ESC fate.
Figure 4B:
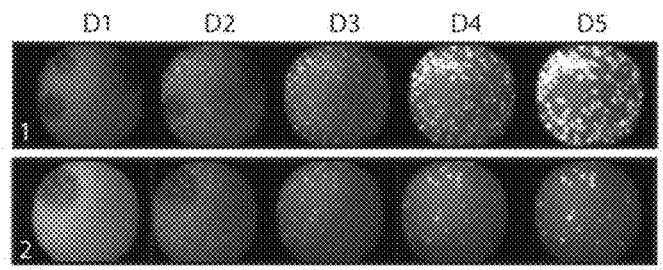
Figure 4C:
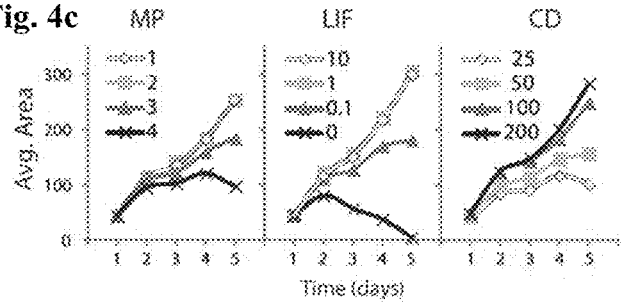
Figure 4D:
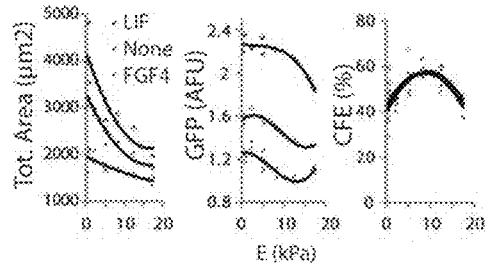
Figure 4E:
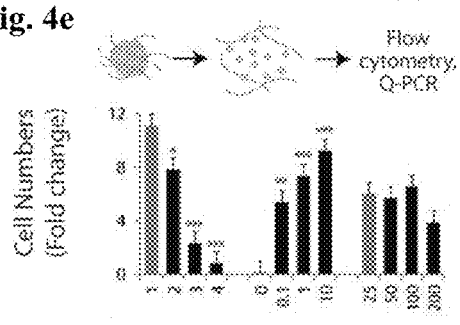
Figure 4F:
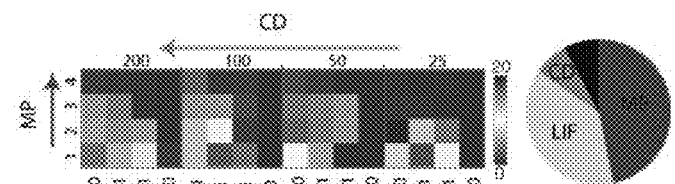
Figure 4G:
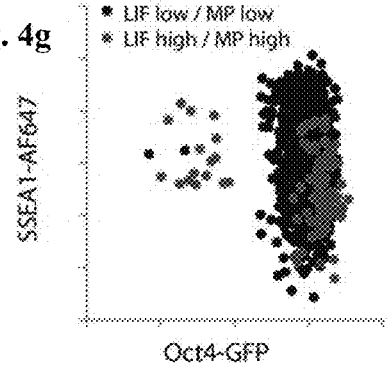
Figure 4H:
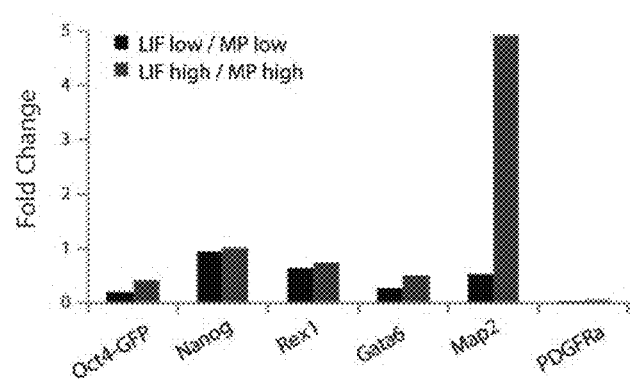

Hereinbelow, embodiments of the invention will be presented in greater detail, by means of embodiments.

Generation of Arrays of 3D Signaling Cell Culture Microenvironments from a Tool-Kit of Molecular Building Blocks To realize the three-dimensional screening of cellular microenvironments according to the present invention it has proven useful to engineer a biomaterials system composed of a library of molecular building blocks which can be independently mixed and then cross-linked in the presence of cells to potentially form a huge diversity of three-dimensional cell microenvironments with distinct and independently controllable properties. It was found that the invention can preferably be carried out on the basis of synthetic hydrogels as biomimetic three-dimensional cell microenvironments with very well defined biochemical and mechanical properties (Lutolf and Hubbell, 2005). Preferably, the coagulation enzyme activated transglutaminase factor XIIIa (FXIIIa) is used in the context of the present invention to crosslink multiarm poly(ethylene glycol) (PEG)-based pre-polymers into 3D hydrogel networks under physiological conditions (cf. FIG. 1a) (Ehrbar et al., 2007). Indeed, it was found that single mouse ESC encapsulated within such PEG-based hydrogels show a very good viability (89.1±7.3%) that is not significantly different (p=0.44) from standard culture conditions on gelatin-coated plastic (92.5±3.6%); results not shown in detail. Gel-encapsulated single ESGs are physically separated from each other from the beginning of an experiment and remain so over time, thereby expanding as clonal entities. To allow for efficient growth in three dimensions, the gels can be rendered susceptible to cell-secreted proteolytic remodeling by designing gels bearing a protease substrate site for degradation (Lutolf et al., 2003; Patterson and Hubbell, 2010) (cf. FIG. 1a). Moreover, biologically active molecules such as oligopeptides or proteins can be site-specifically attached to the matrix during cross-linking (FIG. 1a). This molecular "tool-kit" for making various hydrogel matrices effectively permits to probe a very large combinatorial space of different 3D cellular microenvironments.

As a proof-of-principle, five key signal types of the three-dimensional in vivo microenvironments were prepared where each of these characteristics could be independently varied (cf. FIG. 1b): matrix mechanical properties (abbreviated with "MP"), susceptibility to proteolytic degradation ("DG"), extracellular matrix-derived proteins ("EC"), cell-cell interaction proteins ("CC") and soluble factors ("SF"). By varying the polymer consent, the stiffness (represented by Young's moduli, E) of the gels were specified between ca. 300 and 5400 Pa (Ehrbar et al., 2011) (FIG. 1b) which is in the physiologically relevant range of soft tissues (Engler et al., 2006). The gels were rendered differently degradable by matrix metalloproteinases (MMP) via the incorporation of peptides of different sensitivities (i.e. k cat/K m) to cell-secreted MMPs (Lutolf et al., 2003). Importantly, to perfectly match the mechanical properties of gels that are crosslinked by different MMP substrate peptides, the precursor content was adjusted. Thus, key mechanical and biochemical properties of this synthetic gel system were independently controlled. To systematically modulate the cell signaling properties of the matrices, a set of ECM and recombinant growth factor proteins was chosen which had previously been implicated in regulating ESC pluripotency, and which were enzymatically tethered to the gels in the context of the present invention (cf. FIG. 1b). ESC interaction with laminin, fibronectin and collagen IV had previously been associated with a loss of pluripotency in 2D (Prudhomme et. al., 2004). However, ligation of their integrin homodimers by peptide analogs in a three-dimensional culture system indicated that they could instead promote maintenance of self-renewal (Lee et al., 2010). In addition, an increasing body of work has pointed to transmembrane proteins involved in cell-cell signaling as mediators of self-renewal: E-Cadherin, EpCam and Jagged have been chosen here as representative examples (Andrews et al., 2008; Gires et al., 2009; Soncin et al., 2003). Finally, the soluble ESC regulatory factors leukemia inhibitory factor (LIF), bone morphogenetic protein 4 (BMP4) and fibroblast growth factor 4 (FGF4) (Prudhomme et al., 2004; Qi et al., 2004; Ying et al., 2003) were employed to a serum-free medium formulation such that they could reach the encapsulated cells via the diffusive properties of the gel network. In the present embodiments, four levels of modulation for each of the five categories were specified, leading to a total parameter space of 1024 unique conditions (cf. FIG. 1c). Additionally, cell density, increasingly recognized as an important modulator of ESC fate by autocrine effects, could be prescribed in this experimental, setup as well as retrospectively imaged as demonstrated below.

This level of complexity in formulating three-dimensional cell-containing matrices, as well as the required repetitions, is preferably reduced to practice by miniaturizing the sample volumes and adapting automated methods for gel fabrication (cf. FIG. 1c) and cell fate analysis (cf. FIG. 1d). Specifically, a commercially available liquid handling robot was used to accurately synthesize one µl of each of the unique conditions in triplicate, in a completely automated manner, onto glass slides (not shown) or into standard 1536-well plates (not shown). The latter format was chosen as it presented an ideal surface to volume ratio for the selected hydrogel drops and represented a standard format which could be adapted to various experimental setups. Once the three-dimensional gel array is generated, the system can function as a multimodal assay platform, where multiple readouts can be obtained in parallel.

ESC Fate is Highly Dependent on the Composition of the 3D Cell Culture Microenvironment In order to obtain quantitative information on ESC self-renewal and differentiation in response to the above three-dimensional cell culture microenvironment array, an Oct4-GFP reporter cell line was used, in conjunction with automated imaging and image analysis (cf. FIG. 1d). The transcription factor Oct4 is widely considered as a marker of ESC pluripotency (Niwa et al., 2000). Cells embedded in three-dimensional matrices were imaged the day following seeding to obtain the actual initial number of cells for each well. In the most permissive conditions, these cells formed spherical colonies within three days, and kept proliferating until fixation after five days (cf. FIG. 1d, left panel). Confocal microscopy confirmed that colonies growing in these conditions were in a true three-dimensional space of approximately 500 µm in thickness (cf. FIG. 1d, middle panel). Automated imaging of the complete 3D architecture of the hydrogel was combined with an efficient image analysis pipeline to obtain a number of morphological readouts. Colony area was taken as a measure of proliferation, and GFP intensity as a measure of ESC pluripotency (cf. FIG. 1d, right panel).

For every unique combination of matrix effectors (i.e. MP, DG, EC, CC and SF), colony area and GFP intensity were calculated as the average of three replicates. Each averaged value was represented as a square and given a color (with red representing relative high values and blue representing relative low values) and all values/squares were organized by input condition thereby generating a heat map representation (cf. FIG. 2a). In general, soluble factor modulation was found to be the strongest predictor of heat map intensity, with the LIF condition leading to both high proliferation and self-renewal, with the opposite effect for FGF4 and BMP4, and an intermediate regime appearing for the conditions with no soluble factors. The top ten self-renewing and proliferating conditions were all within the LIF condition, and most tended to be in the conditions of low mechanical properties and absence of cell-cell interaction proteins. Indeed, when all cell culture microenvironments were plotted as colony area versus GFP intensity (cf. FIG. 2b), three populations emerged that were identified as cell culture microenvironments containing LIF, no factors ("None") and BMP4/FGF4, with very little overlap between them. The LIF dependence proved to be a strong biological validation of the platform, as LIF is known to be a critical signal to maintain ESC pluripotency and self-renewal via phosphorylation of the transcription factor signal transducer and activator of transcription (STAT) 3 (Niwa et al., 1998). Additionally, distinct area vs. GFP relationships emerged out of such a representation, suggesting that the correlation between self-renewal and proliferation is linked to a particular soluble factor regime; for FGF/BMP, irrespective of growth characteristics, self-renewal was lost, while with LIF proliferation was strongly correlated to self-renewal. In cell culture microenvironments devoid of any exogenous soluble factors, self-renewing colonies were observed. This is in marked contrast to LIF-free two-dimensional cultures that result in rapid loss of ESC pluripotency and points to the potential role of other factors involved in maintaining ESC in three dimensions. Interestingly, the most self-renewing and proliferating (i.e. high GFP, high area) matrix characteristics in all subpopulations were found in conditions of lower matrix stiffness (cf. FIGS. 2c and 2d).

Systems-Level Analyses Reveal Relative and Combinatorial Effects of ESC Fate Determinants in Three Dimensions To quantify in a systematic way how self-renewal and proliferation varied as a function of the signaling cell culture microenvironment, generalized linear models (GLM) were utilized which encompassed all of the five determinants of the cell culture microenvironment and their interactions (cf.

FIG. 3). This approach allowed to explain more than 70% of the variability in the system. By decoupling subtle effects from the more dominant ones, the relative importance of various factors could be quantified (cf. FIG. 3a), establishing a global hierarchy of components affecting ESC fate in three dimensions. Soluble factors accounted for more than 60% of the model variance. Physical properties, including matrix degradability and stiffness, accounted for approximately half of the remaining model variance, and tethered protein and initial cell density effects each accounted for at most 15%.

The role of individual factors was also investigated within these categories (cf. FIG. 3b). BMP4 and FGF4, when presented as single factors in serum-free medium as in the context of the present invention, impaired self-renewal and no other microenvironmental factor could overcome this effect to any significant degree. Degradable matrices favoured self-renewal, but not necessarily proliferation. Thus, the physical parameters of the matrix may not only dictate colony growth but also coordinate stemness. These processes do not always act in parallel and may be mediated by interacting factors. Indeed, ECM proteins tended to increase the size of colonies but decreased Oct4 expression, which matched previous findings in two-dimensional analysis, where laminin and fibronectin was shown to enhance differentiation of ESC (Prudhomme et al., 2004). Surprisingly, cell-cell interaction proteins such as EpCam tended to decrease both proliferation and self-renewal in the present system, although all three chosen proteins had been previously implicated in maintenance of ESC self-renewal in two-dimensional studies (Andrews et al., 2008; Gires et al., 2009; Soncin et al., 2009). This suggests that certain pathways could be differently activated or overridden by other factors in a three-dimensional environment. Synergistic or antagonistic effects between factors which were statistically significant were represented by a network interaction map (cf. FIG. 3c) and as clustered heat maps showing significant pair-wise interactions (FIG. 3d-g). While some interactions such as those involving soluble factors were involved both in self-renewal and proliferation, others were self-renewal-specific (cf. FIG. 3c). For example, the presence of EpCam with all ECM proteins reduced colony growth (FIG. 3e), while the presence of collagen in gels with low cell density enhanced colony growth (FIG. 3f). Thus, ECM proteins, with their role in activating cell adhesion complexes via integrin engagement (Lee et al., 2010), are involved in modulating the purely physical components of the matrix. Overall, the interaction scheme centered around the soluble factors, underscoring their key role in regulating ESC fate even in a three-dimensional environment.

Complementary Assays Uncover Effects of Stiffness on ESC Fate

To study key aspects of ESC regulation in 3D identified by this large-scale screen in more detail, the platform was rendered compatible with complementary downstream cell assays including flow cytometry and quantitative RT-PCR (cf. FIG. 4). The novel read-outs were implemented in more targeted experiments (cf. FIG. 4a) and in a time-lapse mode (cf. FIG. 4b), in order to also shed light on the dynamics of 3D ESC behavior. For instance, the potency of LIF was simultaneously investigated by performing a dose-dependence study, and the effect of mechanical properties was evaluated by widening the stiffness range and retrospectively measuring the stiffness of every gel (not shown), and a wider range of pre-set cell densities was explored (cf. FIG. 4a). Proliferation was maintained in all conditions for the first two days, followed by a strong dependence on all three parameters (cf. FIG. 4c). Notably, LIF maintained its proliferative role in 3D even at a concentration three orders of magnitude less than the 2D standard. It was confirmed that proliferation was directly related to lower matrix stiffness, while an intermediate stiffness was found to be optimal for self-renewal, and colony-forming efficiency (cf. FIG. 4d). This finding is in line with data suggesting that 3D solid stress can control cellular growth at both the macroscopic and cellular levels in multicellular aggregates such as tumor spheroids (Helmlinger et. al., 1997). More recent work has shown that the elasticity of the in vitro substrate can direct stem cell fate (Engler et. al., 2006; Gilbert et al., 2010). The present results obtained in the context of the invention suggest that mechanical properties could play a similar and fundamental role in regulating ESC maintenance in 3D, where optimal properties in the range of those measured in the early blastocyst might be most appropriate (Khalilian et al., 2010; Murayama et al., 2006).

In order to corroborate these findings at the colony-level with single-cell flow cytometry and gene expression data, hydrogel matrices within each well were digested with protease solution while maintaining cellular integrity. Total cell counts by flow cytometry were most closely correlated to a measure of total colony area by imaging (not shown). To better define the role of cell density, the total colony area was normalized by initial cell density: while higher initial cell densities led to larger colonies, this was not reflected in actual cell numbers counted by flow cytometry (cf. FIG. 4e), suggesting that cells within larger colonies may have died. As with image-based data, each condition could be visualized individually; a heatmap representation (cf. FIG. 4f) indicates a clear trend towards a graded bidirectional influence of LIF and MP, an observation reinforced by a global analysis showing the near-equal role of these two factors in influencing cell proliferation and the reduced role of cell density.

An additional advantage of dissociating cells from the gels is the possibility to readily perform immunocytochemisty. For example, staining for SSEA1, a surface marker commonly used as a complementary marker of pluripotency to transcription factors such as Oct4, indicated a wide range of SSEA1 expression even in cases of high Oct4 (cf. FIG. 4g). DSEA1 expression generally reached higher levels in softer matrices, and a SSEA1 high/Oct4 low subpopulation emerged in cases of high LIF and high MP, suggesting that, as a result of changes in mechanical properties and LIF, concentration, some cells have undergone early commitment steps which is reflected by subtle changes in intracellular and extracellular markers of pluripotency.

To demonstrate that cells collected from the gels could be used for essentially any complementary downstream assay, quantitative RT-PCR on selected samples was performed. Such analyses showed how the expression of some genes associated with pluripotency was significantly downregulated Rex1) while others (Nanog) remained largely unchanged as a result of changes in the physicochemical environment, whereas changes in 3D matrix stiffness resulted in significant upregulation of Map2, a gene associated with early neuroectodermal differentiation (cf. FIG. 4h). Taken together, the possibility to perform these multimodal readouts, including time-lapse imaging, flow cytometry and PCR, opens up broad avenues for looking at cellular systems in microarrayed 3D cell culture microenvironments according to the invention.

Systematic Cell Culture Microenvironmental Factor Analysis Reveals a Set of Factors Marking a Signature of Neuroepithelial Differentiation To demonstrate another embodiment of the invention, a similar methodology as described above was used to investigate factors modulating early neural development, particularly ESC-derived neuroepithelial differentiation.

Importantly, beyond quantifying read-outs of proliferation and differentiation, the latter assessed by GFP intensity reporting Sox1 expression, conditions were sought which could recreate the morphological features of neuroepithelial cysts, which have been defined as tissues comprised of bent epithelial cell layers enclosing a lumen (Gin, 2010), including their spherical and neopolarized features.

In order to maintain a wide-ranging parameter space (5 categories×4 factors per category; bat optimize the number of required experimental conditions, the full factorial experimental design was modified to focus on two rounds of 4-category modulation. In the first array, MP, DG, EG and SF were assessed in a full factorial design (with no CC proteins), and in the second, MP, DG, EC, CC were assessed in a similar way, with the soluble factor FGF4 in all conditions.

Quantification of the results was performed using the previously described GLM-based modeling strategy. Soluble factors, dominated by the effect of LIF, contributed more than 74% of the variability observed for colony area, with only small contributions from mechanical properties and MMP-sensitivity (5%) and nearly negligible effects from other factors (data not shown). In contrast, the variability in GFP intensity was attributed to a much wider set of factors: while soluble factors still contributed the largest proportion (32%), cell-cell interaction proteins accounted for 16% of the variance and physical properties (mechanical properties and MMP-sensitivity) accounted for 9% each (cf. FIG. 5a).

The contribution of individual factors to Sox1-GFP intensity was further analyzed to determine which factors would have roles as positive or negative regulator of differentiation, FGF4 was the soluble factor which had the strongest positive effect on GFP, with LIF and BMP4 both strong negative regulators of neuroepithelial fate (cf. FIG. 5b). The lack of any soluble factor led to only a small negative effect on Sox1-GFP expression, indicating that the baseline condition produced a generally neutral effect on cell fate within the tested conditions. For mechanical properties an intermediate-soft range in elasticity promoted highest Sox1-GFP expression. Indeed, a slight negative effect on differentiation appears in soft matrices and a more pronounced negative one in the stiffer conditions (cf. FIG. 5b).

Non-degradable matrix was significantly more permissive to the formation of GFP+ colonies than MMP-sensitive matrices (cf. FIG. 5b). It can be noted that no change in bulk mechanical properties of the matrix over time in any of the synthetic matrices is observed over the 5 days, suggesting that the effect seen is independent of bulk changes in mechanical properties and is therefore experienced at the local cell and colony scale (data not shown).

The effects of ECM proteins on Sox1-GFP expression in this synthetic system were not significant when presented individually, in contrast to expected changes in differentiation profile expected based on ECM-rich natural matrices such as Matrigel. Finally, cell-cell interaction proteins were found to be strong negative regulators of differentiation, In particular Jagged, a ligand activating the Notch pathway, was seen as the strongest negative regulator of GFP expression (cf. FIG. 5b) suggesting that the addition of a factor present at the desired cell fate does not necessarily function as the right cue to lead an undifferentiated cell towards that lineage, and in fact may promote the opposite behavior.

Interactions between factors were seen to contribute 8% of the overall variance of the GFP model, and, based on the mathematical model of all possible category interactions, 5 pair-wise interactions were determined to be statistically significant (cf. FIG. 5c). Soluble factors (SF) interacted with three other categories, both biophysical (MP and DG) as well as biochemical (EC) (cf. FIG. 5f,g,h). These SF interaction effects seem to be systematic across the three categories: FGF4, for example, has an additive effect on all other factors, which could be interpreted simply as a non-linear effect, which is not captured as a main effect in the linear model but whose non-linearity can be captured by such interaction analysis. Similarly, the non-degradable condition also exhibits such a non-linear effect, but the Ecad condition had a positive influence in the presence of the highly degradable condition (cf. FIG. 5d). Similarly, ECad has a more pronounced positive effect in one of the stiffer conditions (cf. FIG. 5e).

Figure 6A:
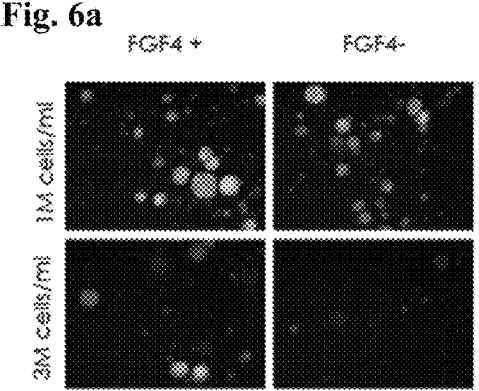
FIG. 6a-d: Images of high throughput-screening.

Screened Conditions Provide a Basis for Mechanistic Insights into Neuroepithelial Morphology and Polarity High-throughput screens such as the one presented here can serve as hypothesis-generating tools for more targeted studies. For example, the putative non-linear effect of FGF4, identified by factor interaction analysis, was shown to be cell-density mediated: at relatively high cell density (3 million cells/ml), the addition of FGF4 to the medium had little effect, whereas at lower cell density (1 million cell/ml), the lack of FGF4 led to loss of proliferation and GFP intensity (cf. FIG. 6a), underscoring the role of this growth factor as an autocrine regulator of neural differentiation.

Figure 6B:
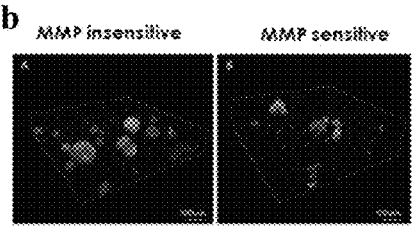

Analysis of the image set from such a screen also outputs additional metrics beyond average colony area as a measure of proliferation and Sox1-GFP expression as a measure of differentiation, with morphological metrics being particularly relevant to relate observed phenotypes to input cell culture microenvironments. By employing a clustering approach to combine multidimensional outputs into clusters of linked morphology, proliferation and differentiation (not shown), a phenotypical signature can be constructed which provides a more complete picture of cellular behavior. As such, it was possible to determine that characteristic smooth, round colonies were generated almost exclusively in non-degradable conditions, whereas colonies maintain high GFP expression but with more eccentric and stellate shapes were present in the degradable matrices (cf. FIG. 6b). In further experiments (not shown) using broadband MMP inhibitors, it was ascertained that this phenomenon was indeed protease-mediated. Thus, by broadening the metrics of interest so include morphological features, it was possible to identify particular microenvironmental conditions inducing different morphologies which may be linked to specific morphogenetic pathways.

Figure 6C:
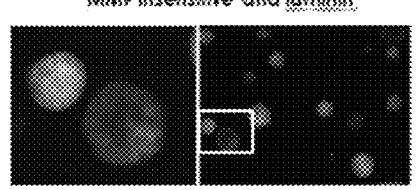
Figure 6D:
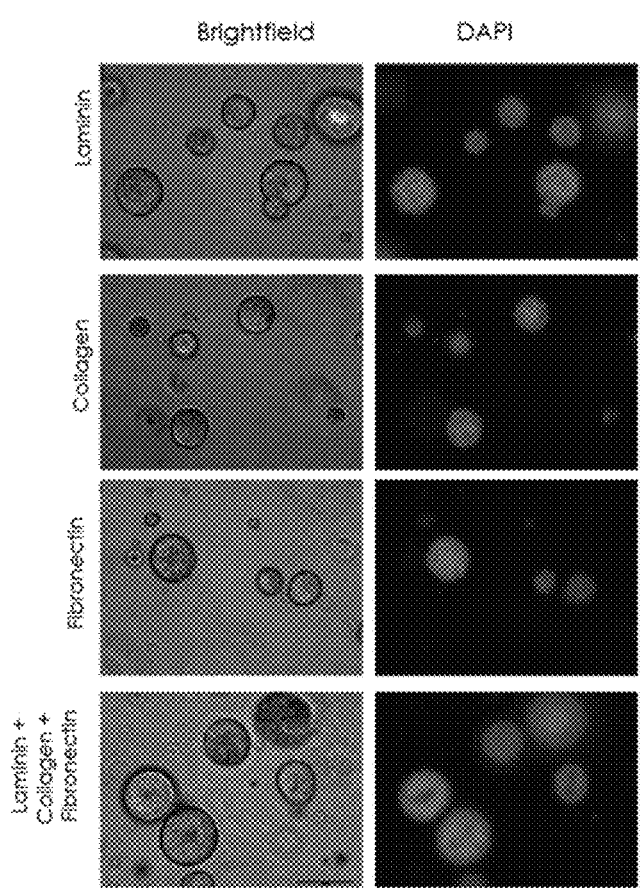

One of the hallmarks of neural cyst formation is the development of a lumen. Confocal 3D reconstructions clearly showed that colonies were indeed well distributed throughout the thickness of the gel, and demonstrated no particular planar bias (cf. FIG. 6b). Colonies growing in close proximity in 3D configuration in the non-degradable gels did not fuse but maintained a thin hydrogel boundary between each other (cf. FIG. 6b), suggesting that growth in such matrices was accomplished by outward force against the matrix and not by any remodelling process. Most significantly, a measure of apico-basal polarity (cf. FIG. 6c) and the beginnings of possible involution was observed in selected conditions characterized by non-degradable matrix and FGF4. Further experiments revealed that while in conditions where single ECM factors were present only infrequent cyst polarity was evidenced, when all three ECM components (laminin, collagen IV and fibronectin) were all incorporated into the matrix, robust and frequent polarity was established (cf. FIG. 6d).

In this high-throughput approach, the response of ESC in arrays of 3D cell culture microenvironments yielded new insights into the regulation of neuroepithelial differentiation. As in the ESC self-renewal study, soluble factors played a predominant role, particularly in determining proliferation, and had a clear effect in either promoting or impeding differentiation. Matrix effects, notably matrix MMP sensitivity, played an equally significant role in specifying cell fate. Indeed, spherical neuroepithelial colonies were only observed in non-degradable matrices, while in degradable matrices, the extent of differentiation and colony morphology were significantly altered. Furthermore, proteins involved in cell-cell interactions impaired neuroepithelial differentiation, while ECM proteins played a significant role in establishing apico-basal polarity only presented in combinatorial manner. A high-throughput platform such as the one deployed here is therefore seen not only as a tool for understanding cell culture microenvironmental influences on developmental pathways, but also as a tremendous hypothesis-generating process which can lead to elucidation of more complex mechanisms.

Arraying Platform is Amenable to Multiple Assays and Cell Types

Figure 7A:
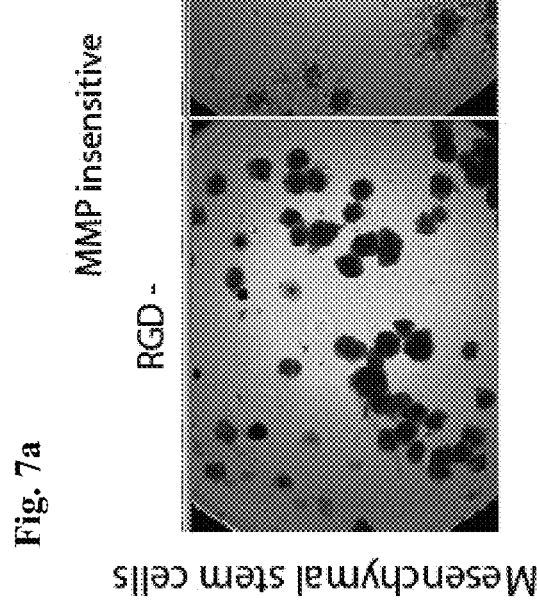
FIG. 7a: Cell-assays of aggregated cells, incorporated in combinatorial cell culture microenvironment.
Figure 7B:
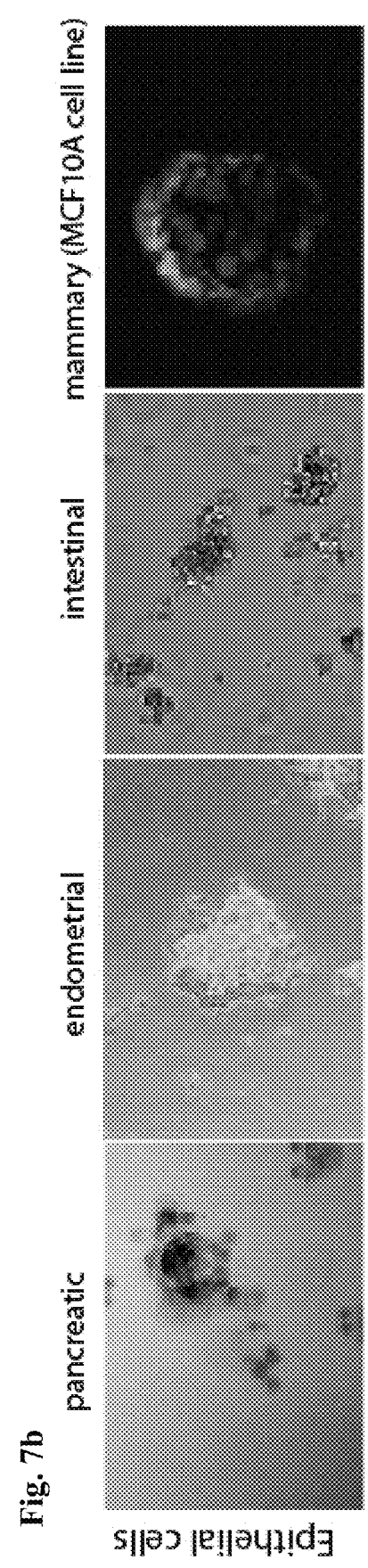
FIG. 7b : a variety of epithelial cell clusters, including pancreatic, endometrial, intenstinal or mammary, incorporated into a screening platform and assessed for stem cell markers, polarity or toher morphological features.

Additional embodiments of the invention include the possibility of conducting migration and morphological assays. Furthermore, such assays can be performed starting from single cells (as seen previously) or from cell aggregates formed in vitro (e.g. embryoid bodies) or isolated directly from live tissue. As an example, mesenchymal stem cells were aggregated, to a size of 300 cells, incorporated in combinatorial cell culture microenvironments, and their migration was assessed after 16 hours (in the presence of PDGF as a soluble factor in the medium). Both matrix-tethered ECM-mimicking peptides (fibronectin derived RGD motif), as well as matrix MMP sensitivity modulated the migration response of cells outward from the cluster (cf. FIG. 7a). A variety of epithelial cell clusters, including for example pancreatic, endometrial, intestinal or mammary, could be incorporated into the screening platform, and assessed for stem cell markers, polarity or other morphological features (cf. FIG. 7b).

Experimental Details

Hydrogel Precursor Synthesis

PEG vinylsulfone (PEG-VS) was produced and characterized as described elsewhere (Lutolf and Hubbell, 2003). In a second step, PEG-VS was functionalized with Factor XIIIa-peptide substrates via a Michael-type addition. A glutamine-containing peptide (NQEQVSPL-ERCG-NH$_2$) and different types of lysine-containing peptides with various MMP sensitive sequence were used: AcFKGG-GPQGI-WGQ-ERCG-NH$_2$ (peptide W), AcFKGG-GDQGIAGF-ERCG-NH$_2$ (peptide A), AcFKGG-PQGIAGQ-ERCG-NH$_2$ (peptide G), AcFKGG-VPMSMRGG-ERCG-NH$_2$ (peptide V). Consequently, one glutamine-PEG precursor (Q-PEG) and four different lysine-PEG precursors were obtained: W-PEG, A-PEG, V-PEG, G-PEG. Functionalization and characterization of these precursors was performed as described elsewhere (Ehrbar et al., 2007). In brief, peptides were added to PEG-VS in a 1.2-fold molar excess over VS groups in 0.3 M triethanolamine (pH 8.0) at 37° C. for 2 h, followed by dialysis (Snake Skin, MWCO 10k, PIERCE) against ultrapure water for 4 days at 4° C. After dialysis, the salt-free products (Q-PEG, W-PEG, A-PEG, V-PEG, G-PEG) were lyophilized to obtain a white powder.

Hydrogel Preparation

Factor XIII (Fibrogammin P, CSL Behring) was reconstituted in water from lyophilized powder to a concentration of 2000/ml. 1 mL of factor XIIIa was activated with 100 µL of thrombin (20 U/mL, Sigma-Aldrich, Switzerland) for 30 min at 37° C. Aliquots of activated factor XIIIa were stored at −80° C. for further use. Precursor solutions to give hydrogels with a final dry mass content ranging from 1.5 to 4% were prepared by stoichiometrically balanced ([Lys]/[Gln]=1) solutions of Q-PEG and each of the four lysine-PEGs in Tris-Buffer (TBS, 50 mM, pH 7.6) containing 50 mM calcium chloride. The cross-linking reaction was initiated by 10 U/mL thrombin-activated factor XIIIa and vigorous mixing. To obtain disc-shaped matrices, the liquid reaction mixtures (50 µL) were sandwiched between sterile hydrophobic glass microscopy slides (obtained by treatment with SigmaCote, Sigma) separated by spacers (ca. 1 mm thickness) and clamped with binder clips. The matrices were then incubated for 30 min. at 37° C.

Characterization of MMP-Mediated Degradation

Three 50 µl gel disks at 3.5% w/v PEG were made for each of the 4 peptide sequences and allowed to swell for 12 hours in 50 mm Tris, 100 mM NaCl, 10 mM CaCl$_2$ buffer at ph 7.5. They were then weighted and placed in a 40 mM MMP-1 solution, dissolved in the same buffer. The gel mass was recorded at 2-hour intervals for the first 12 hours, then at t=18, 24, 48 and 72 hrs. The time to complete degradation was determined either directly or by linear regression (for G peptide) and inverted to give a measure of degradability.

Characterization of Mechanical Properties

Gel disks (n=3 for each MMP sensitivity) were allowed to swell in buffer for 12 hours and small strain oscillatory shear rheometry was then performed. Swollen hydrogel discs of 1 to 1.4 mm thickness were sandwiched between the two plates of a Bohlin CV 120 rheometer (Bohlin Instruments), with compression up to a range between 85% to 75% of their original thickness to avoid slipping. Measurements were then conducted in constant strain (5%) mode. Shear stress was recorded over the frequency range of 0.1 to 1 Hz and average storage moduli G' over the frequency range were obtained. Storage modulus (G') was plotted as function of hydrogel % PEG w/v for each of the 4 MMP-sensitivities. Linear interpolation was performed on the G' vs. % PEG data points. The % PEG corresponding to 0, 600, 1200 and 1600 Pa was determined for each degradability.

Modification of Matrices with Cell-Cell Interaction Proteins

To bind cell-cell interaction proteins to the hydrogel network, a Fc-tag/Protein A conjugation strategy was used. To render Protein A susceptible for Factor XIIIa-catalyzed crosslinking, a Q-containing peptide was linked to the Protein A using NHS-PEG-maleimide, a heterobifunctional PEG linker. The modification of Protein A was achieved in a two-step reaction: functionalization with maleimide group by reaction of NHS-PEG-maleimide in 10-fold molar excess, followed by Q-peptide attachment via its cysteine side chain. Consequently, the Q-Protein A-functionalization was qualitatively assessed by SDS-PAGE. A fluorescent counter-reactive substrate for Factor XIIIa, lysine-containing probe, Lys-Tamra, was chosen for detecting if a Factor XIIIa-mediated crosslinking reaction can occur. Upon mixing of Protein A and Lys-Tamra in the presence of Factor XIIIa, a fluorescent signal corresponding to Protein A was detected on SDS-PAGE and in-gel fluorescence scanning, demonstrating successful bioconjugation. In order to achieve covalent tethering of cell-cell interaction proteins into Factor XIIIa-based hydrogels, Fc-tagged E-Cadherin, EpCAM and Jagged (R&D Systems) were premixed with Q—Protein A in a 1.66 molar excess ratios for 30 min at room temperature. Considering the fact that Protein A has five Fc-binding sites, we have afforded 3 times molecular excess of each Fc-binding sites with respect to a Fc-protein, which should ensure optimal immobilization of morphogens. The obtained solution of fully functional proteinaceous constructs were aliquoted and stored at −20° C. until further use.

Determination of ECM Proteins Susceptibility for Factor XIIIa-Mediated Crosslinking Based on the hypothesis that large-sized ECM proteins could be natural substrates for Factor XIIIa and would tether to the hydrogel network without further conjugation, the following ECM proteins of interest in solution were used: Laminin, collagen I (BD Biosciences), fibronectin (R&D Systems). A fluorescent binding assay was performed, in which proteins were mixed with each of fluorescent Factor XIIIa substrates (Q-peptide-Alexa647 or Lys-Tamra) in the presence of Factor XIIIa. The reactions were qualitatively analyzed by SDS-PAGE and in-gel fluorescence scanning, demonstrating that indeed the proteins are susceptible for Factor XIIIa-based crosslinking. All ECM proteins were aliquoted at 4° C. and stored at −20° C.

Cell Culture

In all ESC self-renewal experiments Oct4-GFP mouse embryonic stem cells (mESC) (R1 line provided by Zandstra lab) were routinely cultured on gelatin-coated dishes in medium containing 15% serum (Hyclone) and 106 U/ml LIF (Millipore). Twelve hours prior to the experiment, the medium was changed to serum-free knock-out medium (KO).

In all neuroepithelial differentiation experiments Sox1-GFP mouse embryonic stem cells (46C cell line provided by Tanaka lab) were routinely cultured in medium containing 15% serum (Hyclone) and $10^6$ U/ml LIF (Millipore). Before the experiment, cells were trypsinized and resuspended in neural differentiation medium devoid of any induction cues. The N2/B27 formulation was as reported elsewhere (Ying, 2003).

In all mesenchymal stem cell migration experiments, primary multipotent mesenchymal stem cells from human placenta (cells used at Passage 8, provided by Ehrbar lab), were routinely cultured at in medium containing 15% serum (Invitrogen). Aggrewell plates (STEMCELL Technologies SARL) were used to generate cell aggregates of 250 cells each, which were then harvested and used in gel encapsulation experiments. To stimulate migration in the assay, 50 ng/ml PDGF (Peprotech) was added to the basal medium.

Experiments with mammary epithelial cells were carried out using MCF10A cell line, routinely cultured in growth medium and differentiated as described elsewhere (Debnath, 2003). Primary epithelial cell aggregates were isolated and differentiated using standard techniques and reagents, as outlined elsewhere (Jin, 2013; Schatz, 2000; Li, 2012; pancreatic, endometrial, intestinal, respectively), Viability Assay A viability assay was carried out to compare cell behaviour in 2D and 3D conditions. Wild-type mESCs were trypsinized and seeded on gelatin-coated tissue culture dish (2D) or encapsulated in a 600 Pa non-degradable (A) hydrogel disk (3D) at 1 M cells/ml. Incubation at 37° C. 5% $CO_2$ was carried out for 4 hours in +LIF serum-free conditions, followed by staining with LIVE/DEAD Cell Viability Assay, following the manufacturer's instructions. Conventional (2D) or confocal (3D) fluorescence imaging was carried oat, followed by manual counting of the proportion of live (green) vs. dead (red) cells was carried out on three independent samples.

Robotic Mixing and Dispensing

In order to achieve the combinatorial complexity of this approach a Hamilton Microlab StarPlus automatic liquid handling robot with Nanopipettor head was used. All automated steps were programmed with MicroLab Vector Software version 4.1.1 (HAMILTON Bonaduz A G, Switzerland). Stock solutions of premixed stoichiometrically balanced PEG solutions corresponding to the four peptides were prepared by mixing glutamine-PEG precursor (Q-PEG) with the four different lysine-PEG precursors: W-PEG, A-PEG, V-PEG, G-PEG. Each of these four stock solutions was diluted to the rheology-determined four corresponding concentrations required to achieve matched target stiffnesses. The dilution and all subsequent steps of the process were performed robotically, with fluid handling parameters optimized for every material class and checked by mass measurement on a balance (data not shown). Importantly, 30% of the total final volume was left empty (spare volume) to account for subsequent addition of proteins, cells and Factor XIIIa (10% of total volume for each component). These 16 combinations were aliquoted into 236 wells of a 384-well plate. EC and CC proteins were thawed on ice, diluted to a concentration of 500 nM, and placed into the wells of a cooled 384 well plate. The four EC proteins (including blank control) were dispensed into the 236 gel precursor-filled wells, followed by the four CC proteins, in an orthogonal manner such as to obtain at the end of this step 256 unique combinations of MP, DG, EC and CC (4×4×4×4). A 96 well plate was prepared with the mediums containing three soluble factors and a blank control: FGF4, BMP4 at 10 ng/ml (R&D Systems) and LIF at 106 U/ml (Millipore). Cells were trypsinized and resuspended in a serum-free medium at a concentration of 1×106 cells/ml and kept on ice. Simultaneously, frozen aliquots of Factor XIIIa were thawed and also kept on ice. Then in a sequential fashion, cells were dispensed into eight wells of the mixed gel precursors, quickly followed by dispensing and robotic mixing of Factor XIIIa. Immediately following the addition of Factor XIIIa, and, before onset of gelation (circa 2-3 min), the 8-channel Nanopipettor was used to aspirate 12.5 µl from each well and dispense 1 µl in 12 wells of a 1536 well plate. This process was repeated a total of eight times per 1536 plate (12×8 channels×8 times×12 drops/(channel·time)=768 drops) to fill half of a 1536 well plate. Throughout the process the 1536 well plate was cooled to 4° C. to prevent evaporation. At the end of the gel dispensing round, the 4 different mediums in the 96 well, plate were dispensed into the 1536 experiment plate. The medium dispense steps were also carried out sequentially and were synchronized such that all gels were allowed to cross-link for approximately 30 minutes. Overall the process from trypsinization to completion of the medium dispense took two hours, and was carried out four times for the entire experiment (4×4 half-plates of 1536 wells=3072 wells).

For the neuroepithelial differentiation experiments, in a first array, soluble factor modulation was performed with all other combination except cell-cell interaction proteins. In a second array, all cell-cell interaction proteins were tested against all other conditions other than soluble factors, which was limited to the FGF4 condition. This soluble factor regime was chosen as it has been reported to be most favorable for neuroepithelial differentiation[2], particularly in situations of low cell density where autocrine feedback mechanisms are reduced. In this study, in order to identify the role of extrinsic factors independently of autocrine mechanisms, we imposed a relatively sparse initial cell density of 200 cells/μl, with daily medium exchanges.

In Situ Measurement of Mechanical Properties

In experiments focusing on mechanical properties, a technique was developed to measure stiffness by indentation in each of the 384 wells (not shown). A compression tester (TA.XTPlus Texture Analyze, Stable Micro Systems Ltd) was fitted with a custom-made 1.5 mm diameter indenting tip. Force was recorded between 0 and 70% strain. Young's modulus was calculated from the slope of the curve between 20 and 30% strain (Elow), using the equation: $E=2ad/F(1-v^2)$, where a is the radius of the indentor tip cylinder (0.75 mm), d is the indentation depth in mm, F is the recorded force in N, and v is Poisson's ratio, taken to be 0.5.

Gel Dissociation, Flow Cytometry and Gene Expression Analysis

Gels in the 384 well plate were washed with PBS for 30 minutes, then incubated at 37° C. with TrypLE Express (Invitrogen) cell dissociation solution for three cycles of 30 minutes. After each cycle, cells were collected, transferred to a round bottom 96 well plate and kept at 4° C. At the end of the process wells were washed with serum-containing medium. In cases where antibody staining was carried out, SSEA-1-AlexaFluor647 (EBiosciences) was used according to the manufacturer's instructions. Cells were analyzed using an Accuri C6 flow cytometer (BD Biosciences). For PCR, cell dissociation was carried out with TrypleE Express as above, RNA was isolated using Tripure Isolation Reagent (Roche) according to the manufacturer's instructions, cDNA was synthesized using iScript Select cDNA synthesis kit (BioRad) and RT-PCR was carried out with iQ SYBR Green Supermix (BioRad) on a Applied Biosystems 7500 machine.

Imaging

All imaging was carried out on a BD Pathway 435 automated imaging system (BD Biosciences). Imaging was performed on plates with live cells at D1 in the GFP channel. Plates were fixed with 4% paraformaldehyde and stained with DAPI at D5, followed by imaging in the GFP and DAPI channels. A 4× objective (Olympus UP-lan FLN N.A. 0.13) was used such that an entire well could be captured in a single field of view. Even at this low resolution, single cells at D1 could be distinguished. At every xy position, i.e. for every well, six images were captured across a z-stack height of 800 μm. For each well, these six images in each channel were collapsed into a single additive image. The 3D information content of an entire experiment was obtained within less than four hours.

Image Analysis

All images from the ESC self-renewal study were processed using algorithms developed in CellProfiler v.9777 (Broad Institute). For D1 analysis: Collapsed image stacks for each well in the GFP channel were input. Images were thresholded and segmented. The number of cells per well was the only readout of interest here. All segmentations were validated by visual inspection. For D5 analysis: Collapsed image stacks for each well in the GFP and DAPI channel were input. DAPI images were thresholded and segmented. Identified colony areas in DAPI were used as masks for the GFP images. For each colony, area (in pixels), average (across colony pixels) DAPI Intensity and average GFP intensity was recorded.

All images from the neuroepithelial differentiation study were processed using algorithms developed in CellProfiler v. 11710 (Broad Institute). In brief, collapsed image stacks for each well in the GFP and DAPI channel were input. DAPI images were thresholded and segmented using the Otsu Adaptive segmentation algorithm. Colonies were identified as those covering an area above 8 pixels (i.e. smaller colonies were discarded from further analysis). Identified colony areas in DAPI were used as masks for the GFP images. For each colony, shape metrics were obtained from this segmentation process and the DAPI and GFP colony intensity metrics for these colonies were obtained from the original, unprocessed images. All segmentations were validated by visual inspection.

Data Processing

Matlab R2010b (Mathworks) and Matlab R2010b was used to process and visually explore the data. Number of colonies at D1 and D5, as well as the number of colonies, average colony area (in pixels) and average GFP and DAPI intensity (in arbitrary fluorescence units), all at D5, were calculated by averaging single colony data for each well (3072 data points) and for each unique condition (1024 data points). GPP Intensity was normalized to DAPI intensity, and the area was converted from pixels to $mm^2$. The data was further centered around the mean and rearranged by input conditions to obtain the heat maps represented in FIG. 2.

Statistical Analysis

Data from the individual conditions was input into R V2.11. For colony area and normalized GFP intensity, GLM (generalized linear models) models, which took into account all possible interaction terms were specified. The step AIC procedure was run to obtain optimal models based on the Akaike criterion. The GLM procedure of SAS v9.0 software (SAS Institute) was used to test the significance of colony area variation. Differences of LS means±standard errors with the control were tested for significance. The same procedure was used to explain the variability of GFP Intensity. The used models considered the effects of MP, DG, CC, EC and SF, as well as interactions determined to be significant. For all parametric tests, normality of the residues and homogeneity of the variance were examined in QQ and Tukey-Anscombe plots respectively. Log transformations were utilized to improve the normality of the residues. The network interaction map, where node size was linearly proportional to the product of normalized area and normalized GFP intensity, was constructed in Cytoscape (USCD), and the interaction matrices and clustering was performed in MeV v.4.4 (TM4 Microarray Suite).

REFERENCES

Andrews, P. W., Fox, V., Gokhale, P. J., Walsh, J. R., Matin, M., and Jones, M. (2008). Cell-cell signaling through NOTCH regulates human embryonic stem cell proliferation, Stem Cells 26, 715-723.

Debnath, J., Muthuswamy, S. K. & Brugge, J. S. Morphogenesis and oncogenesis of MCF-10A mammary epithelial acini grown in three-dimensional basement membrane cultures. Methods 30, 256-268, (2003).

Ehrbar, M., Rizzi, S. C., Schoenmakers, R. G., Miguel, B. S., Hubbell, J. A., Weber, F. E., and Lutolf, M. P. (2007). Biomolecular hydrogels formed and degraded via site-specific enzymatic reactions. Biomacromolecules 8, 3000-3007.

Ehrbar, M., Sala, A., Lienemann, P., Range, A., Mosiewicz, K., Bittermann, A., Rizzi, S. C., Weber, F. E., and Lutolf, M. P. (2011). Elucidating the role of matrix stiffness in 3D cell migration and Biophys J 100, 284-293.

Engler, A. J., Sen, S., Sweeney, H. L., and Discher, D. E. (2003). Matrix elasticity directs stem cell lineage specification. Cell 126, 677-689.

Flaim, C. J., Chien, S., and Bhatia, S. N. (2005). An extracellular matrix microarray for probing cellular differentiation. Nat Methods 2, 119-125.

Gilbert, P. M., Havenstrite, K. L., Magnusson, K. E., Sacco, A., Leonardi, N. A., Kraft, P., Nguyen, N. K., Thrun, S., Lutolf, M. P., and Blau, H. M. (2010). Substrate elasticity regulates skeletal muscle stem cell self-renewal in culture. Science 329, 1078-1081.

Gin, E., Tanaka, E. M., & Brusch, L. A model for cyst lumen expansion and size regulation via fluid secretion. J Theor Biol 264, 1077-1088, (2010).

Gires, O., Gonzalez, B., Denzel, S., Mack, B., and Conrad, M. (2009). EpCAM Is Involved in Maintenance of the Murine Embryonic Stem Cell Phenotype. Stem Cells 27, 1782-1791.

Gobaa, S., Hoehnel, S., Roccio, M., Negro, A., Kobel, S., and Lutolf, M. P. (2011). Artificial niche microarrays for probing single stem cell fate in high throughput. Nat Methods 8, 949-955.

Griffith, L. G., and Swartz, M. A. (2006). Capturing complex 3D tissue physiology in vitro. Nat Rev Mol Cell Biol 7, 211-224.

Helmlinger, G., Netti, P. A., Lichtenbeld, H. C., Melder, R. J., and Jain, R. K. (1997). Solid stress inhibits the growth of multicellular tumor spheroids. Nat Biotechnol 15, 778-783.

Jin, L. et al. Colony-forming cells in the adult mouse pancreas are expandable in Matrigel and form endocrine/acinar colonies in laminin hydrogel. Proc Natl Acad Sci USA 110, 3907-3912, (2013).

Khalilian, M., Navidbakhsh, M., Valojerdi, M. R., Chizari, M., and Yazdi, P. E. (2010). Estimating Young's modulus of zona pellucida by micropipette aspiration in combination with theoretical models of ovum. J R Soc Interface 7, 687-694.

Khan, F., Tare, R. S., Kanczler, J. M., Oreffo, R. O. C., and Bradley, M. (2010). Strategies for cell manipulation and skeletal tissue engineering using high-throughput polymer blend formulation and microarray techniques. Biomaterials 31, 2216-2228.

Kraehenbuehl, T. P., Langer, R., and Ferreira, L. S. (2011). Three-dimensional biomaterials for the study of human pluripotent stem cells. Nature Methods 8, 731-736.

LaBarge, M. A., Nelson, C. M., Villadsen, R. Fridriksdottir, A., Ruth, J. R., Stampfer, M. R., Petersen, O. W., and Bissell, M. J. (2009). Human mammary progenitor cell fate decisions are products of interactions with combinatorial microenvironments. Integr Biol (Camb) 1, 70-79.

Lee, S. T., Yun, J. I., Jo, Y. S., Mochizuki, M., van der Vlies, A. J., Kontos, S., Ihm, J. E., Lim, J. M., and Hubbell, J. A. (2010). Engineering integrin signaling for promoting embryonic stem cell self-renewal in a precisely defined niche. Biomaterials 31, 1219-1226.

Li, V. S. & Clevers, H. In vitro expansion and transplantation of intestinal crypt stem cells. Gastroenterology 143, 30-34, (2012).

Lutolf, M. P., and Hubbell, J. A. (2003). Synthesis sod physicochemical characterization of end-linked poly(ethylene glycol)-co-peptide hydrogels formed by Michael-type addition. Biomacromolecules 4, 713-722.

Lutolf, M. P., and Hubbell, J. A. (2000). Synthetic biomaterials as instructive extracellular microenvironments for morphogenesis in tissue engineering. Nat Biotechnol 23, 47-55.

Lutolf, M. P., Lauer-Fields, J. L., Schmoekel, H. G., Metters, A. T., Weber, F. E., Fields, G. B., and Hubbell, J. A. (2003). Synthetic matrix metalloproteinase-sensitive hydrogels for the conduction of tissue regeneration: engineering cell-invasion characteristics. Proc Natl Acad Sci USA 100, 5413-5418.

Mei, Y., Saha, K., Bogatyrev, S. R., Yang, J., Hook, A. L., Kalcioglu, Z. I., Cho, S. W., Mitalipova, M., Pyzocha, N., Rojas, F., et al. (2010). Combinatorial development of biomaterials for clonal growth of human pluripotent stem cells. Nat Mater 9, 768-778.

Murayama, Y., Mizuno, J., Kamakura, H., Fueta, Y., Nakamura, H., Akaishi, K., Anzai, K., Watanabe, A., Inui, H., and Omata, S. (2006). Mouse zona pellucida dynamically changes its elasticity during oocyte maturation, fertilization and early embryo development. Hum Cell 19, 119-125.

Niwa, H., Burdon, T., Chambers, I., and Smith, A. (1998). Self-renewal of pluripotent embryonic stem cells is mediated via activation of STAT3. Gene Dev 12, 2048-2060.

Niwa, H., Miyazaki, J., and Smith, A. G. (2000). Quantitative expression of Oct-3/4 defines differentiation, dedifferentiation or self-renewal of ES cells. Nat Genet 24, 372-376.

Patterson, J., and Hubbell, J. A. (2010). Enhanced proteolytic degradation of molecularly engineered PEG hydrogels in response to MMP-1 and MMP-2. Biomaterials 31, 7836-7845.

Prudhomme, W., Daley, G. Q., Zandstra, P., and Lauffenburger, D. A. (2004). Multivariate proteomic analysis of murine embryonic stem cell self-renewal versus differentiation signaling. Proc Natl Acad Sci USA 101, 2900-2905.

Qi, X., Li, T. G., Hao, J., Hu, J., Wang, J., Simmons, H., Miura, S., Michina, Y., and Zhao, G. Q. (2004). BMP4 supports self-renewal of embryonic stem cells by inhibiting mitogen-activated protein kinase pathways. Proc Natl Acad Sci USA 101, 6027-6032.

Schatz, F., Soderland, C., Hendricks-Munoz, K. D., Gerrets, R. P. & Lockwood, C. J. Human endometrial endothelial cells: isolation, characterization, and inflammatory-mediated expression of tissue factor and type 1 plasminogen activator inhibitor. Biol Reprod 62, (2000).

Schmeichel, K. L., and Bissell, M. J. (2003). Modeling tissue-specific signaling and organ, function in three dimensions. J Cell Sci 116, 2377-2388.

Soen, Y., Mori, A., Palmer, T. D., and Brown, P. O. (2006). Exploring the regulation of human neural precursor cell differentiation using arrays of signaling microenvironments. Mol Syst Biol 2.

Soncin, F., Mohamet, L., Eckardt, D., Ritson, S., Eastham, A. M., Bobola, N., Russell, A., Davies, S., Kemler, R., Merry, C. L., et al. (2009). Abrogation of E-cadherin-mediated cell-cell contact in mouse embryonic stem cells results in reversible LIF-independent self-renewal. Stem Cells 27, 2069-2080.

Yamada, K, M., and Cukierman, E. (2007). Modeling tissue morphogenesis and cancer in 3D. Cell 130, 601-610.

Ying, Q. L., Nichols, J., Chambers, I., and Smith, A. (2003). BMP induction of Id proteins suppresses differentiation and sustains embryonic stem cell self-renewal in collaboration with STAT3. Cell 115, 281-292.

Ying, Q. L., Skavridis, M., Griffiths, D., Li, M. & Smith, A. Conversion of embryonic stem cells into neuroectodermal precursors in adherent monoculture. Nat Biotechnol 21, 183-186, (2003).

The invention claimed is:

1. A method of making an array, wherein the array has discrete volumes of cell culture micro-environments possessing different properties influencing behavior of encapsulated cells, in particular proliferation, colony-formation, differentiation, migration, or combinations thereof, said method comprising:
   a) providing one or more different hydrogel precursor molecules, wherein said hydrogel precursor molecules are branched hydrophilic polyethylene glycol having between 3 and 8 arms with a molecular weight between 10 and 40 kDa, in a concentration range between 1 and 10% (w/v), and at least one crosslinking agent, for building up cell culture micro-environments;
   b) combining and dispensing different combinations of said hydrogel precursor molecules and the at least one crosslinking agent, according to step a), onto discrete volumes of a multi-well plate, made from plastic or glass, in an automated manner;
   c) adding one or more biologically active molecules to said discrete volumes of said multi-well plate and either attaching said biologically active molecules to at least one of said hydrogel precursor molecules present or a hydrogel, formed in step e), or allowing the biologically active molecules to diffuse freely;
   d) adding cells onto/into said discrete volumes of said multi-well plate; and
   e) crosslinking said hydrogel precursor molecules based on an enzymatically catalyzed reaction or a Michael addition reaction to form a hydrogel matrix.

2. The method according to claim 1, further comprising selecting the one or more biologically active molecules, in step c), from the group of consisting of extracellular matrix-derived factors, cell-cell interaction factors and cell-signalling factors.

3. The method according to claim 1, further comprising depending said enzymatically catalyzed reaction, in step e), on activated transglutaminase factor XIIIa.

4. A method of making an array, wherein the array has discrete volumes of cell culture micro-environments possessing different properties influencing behavior of encapsulated cells, in particular proliferation, colony-formation, differentiation, migration, or combinations thereof, said method comprising of:
   a) providing one or more different hydrogel precursor molecules, wherein said hydrogel precursor molecules are branched hydrophilic polyethylene glycol having between 3 and 8 arms with a molecular weight between 10 and 40 kDa, in a concentration range between 1 and 10% (w/v), and at least one crosslinking agent, for building up cell culture micro-environments;
   b) combining and dispensing different combinations of said hydrogel precursor molecules and the at least one crosslinking agent, according to step a), onto discrete volumes of a multi-well plate, made from plastic or glass, in an automated manner;
   c) adding one or more biologically active molecules to said discrete volumes of said multi-well plate and either attaching said biologically active molecules to at least one of said hydrogel precursor molecules present or a hydrogel, formed in step e), or allowing the biologically active molecules to diffuse freely;
   d) adding cells onto/into said discrete volumes of said multi-well plate; and
   e) crosslinking said hydrogel precursor molecules based on an enzymatically catalyzed reaction or a Michael addition reaction to form a hydrogel matrix.

* * * * *